(12) United States Patent
Yamamoto et al.

(10) Patent No.: US 10,073,078 B2
(45) Date of Patent: Sep. 11, 2018

(54) BLOOD COAGULATION ANALYZER HAVING A PLURALITY OF MEASUREMENT SECTIONS

(75) Inventors: Norimasa Yamamoto, Kobe (JP); Kazutoshi Tokunaga, Kakogawa (JP)

(73) Assignee: SYSMEX CORPORATION, Kobe-shi, Hyogo (JP)

(*) Notice: Subject to any disclaimer, the term of this patent is extended or adjusted under 35 U.S.C. 154(b) by 1110 days.

(21) Appl. No.: 11/889,250

(22) Filed: Aug. 10, 2007

(65) Prior Publication Data
US 2008/0044912 A1 Feb. 21, 2008

(30) Foreign Application Priority Data

Aug. 18, 2006 (JP) ................................. 2006-222969

(51) Int. Cl.
*G01N 33/49* (2006.01)
*G01N 21/31* (2006.01)
(Continued)

(52) U.S. Cl.
CPC ....... *G01N 33/4905* (2013.01); *G01N 21/272* (2013.01); *G01N 21/314* (2013.01);
(Continued)

(58) Field of Classification Search
None
See application file for complete search history.

(56) References Cited

U.S. PATENT DOCUMENTS 4,477,190 A * 10/1984 Liston .................. G01N 21/253
356/418

4,528,159 A * 7/1985 Liston ...................... B01L 3/505
356/244
(Continued)

FOREIGN PATENT DOCUMENTS

EP 1840555 A1 10/2007
EP 1840559 A1 10/2007
(Continued)

OTHER PUBLICATIONS

English abstract and machine translation of JP 2006-194744.*
Communication from European Patent Office; Application No. 07015685.6-1554; dated Mar. 2, 2017.

*Primary Examiner* — Christopher Adam Hixson
*Assistant Examiner* — Michelle Adams
(74) *Attorney, Agent, or Firm* — Sughrue Mion, PLLC

(57) ABSTRACT

A blood coagulation analyzer and analyzing method perform following: (a) preparing a measurement specimen by dispensing a blood specimen and a reagent into a reaction container; (b) emitting light of a plurality of wavelengths to the measurement specimen in the reaction container, the wavelengths comprising a first wavelength for use in a measurement by a blood coagulation time method, and at least one of a second wavelength for use in a measurement by a synthetic substrate method and a third wavelength for use in a measurement by an immunoturbidimetric method; (c) detecting light of a plurality of wavelengths corresponding to the light emitted in (b), from the measurement specimen, by a light receiving element, and acquiring data corresponding to each wavelength; and (d) conducting an analysis based on the data corresponding to one of the wavelengths among the acquired data, and acquiring a result of the analysis.

18 Claims, 27 Drawing Sheets

(51) Int. Cl.
  *G01N 21/27* (2006.01)
  *G01N 21/82* (2006.01)
  *G01N 35/02* (2006.01)

(52) U.S. Cl.
  CPC ........... *G01N 21/82* (2013.01); *G01N 35/025* (2013.01); *G01N 2021/3133* (2013.01); *G01N 2021/3137* (2013.01); *G01N 2021/3148* (2013.01); *G01N 2021/3174* (2013.01); *G01N 2021/825* (2013.01); *G01N 2201/0618* (2013.01); *G01N 2201/0826* (2013.01)

(56) References Cited

U.S. PATENT DOCUMENTS

| | | |
|---|---|---|
| 5,002,392 A | 3/1991 | Swope et al. |
| 5,283,178 A * | 2/1994 | Kessler .............. G01N 33/5304 356/39 |
| 5,646,046 A | 7/1997 | Fischer et al. |
| 6,353,471 B1 | 3/2002 | Samsoondar et al. |
| 6,902,703 B2 * | 6/2005 | Marquiss et al. ............. 422/505 |
| 2006/0190187 A1 | 8/2006 | Fischer |
| 2006/0202133 A1 * | 9/2006 | Ok .......................... G01J 3/02 250/458.1 |
| 2007/0222973 A1 * | 9/2007 | Hoshiko et al. ................ 356/39 |
| 2008/0273205 A1 * | 11/2008 | Lee ..................... G01N 21/253 356/440 |

FOREIGN PATENT DOCUMENTS

| | | |
|---|---|---|
| EP | 1845363 A2 | 10/2007 |
| JP | 2002-196007 A | 7/2002 |
| JP | 2006-194744 * | 7/2006 |

\* cited by examiner

| Step of 48 μsec | CH (MUX number) | | |
|---|---|---|---|
| | Line L0 | Line L1 | Line L2 |
| 0 | CH0 (0) | CH16 (0) | CH32 (0) |
| 1 | CH0 (0) | CH16 (0) | CH32 (0) |
| 2 | CH0 (0) | CH16 (0) | CH32 (0) |
| 3 | CH1 (1) | CH16 (0) | CH32 (0) |
| 4 | CH1 (1) | CH17 (1) | CH32 (0) |
| 5 | CH1 (1) | CH17 (1) | CH33 (1) |
| 6 | CH2 (2) | CH17 (1) | CH33 (1) |
| 7 | CH2 (2) | CH18 (2) | CH33 (1) |
| ⋮ | ⋮ | ⋮ | ⋮ |
| 44 | CH14 (14) | CH30 (14) | CH46 (14) |
| 45 | CH15 (15) | CH30 (14) | CH46 (14) |
| 46 | CH15 (15) | CH31 (15) | CH46 (14) |
| 47 | CH15 (15) | CH31 (15) | CH47 (15) |
| 48 | CH0 (0) | CH31 (15) | CH47 (15) |
| 49 | CH0 (0) | CH16 (0) | CH47 (15) |
| 50 | CH0 (0) | CH16 (0) | CH32 (0) |

Multiplexer switching process + standardizing process + amplifying process

Signal waiting process

A/D conversion process + data storing process

BLOOD COAGULATION ANALYZER HAVING A PLURALITY OF MEASUREMENT SECTIONS

CROSS REFERENCE TO RELATED APPLICATION

This application claims the benefit of priority from Japanese Patent Application 2006-222969, filed on Aug. 18, 2006, the entire disclosure of which is incorporated herein by reference.

FIELD OF INVENTION

The present invention relates to blood coagulation analyzers and blood coagulation analyzing methods, in particular, to a blood coagulation analyzer and blood coagulation analyzing method of measuring a measurement specimen, which is a mixture of blood specimen and reagent.

BACKGROUND

Conventionally, a blood coagulation analyzer is known in which the measurement specimen obtained by adding a predetermined measurement reagent to blood plasma is accommodated in a light transparent container, and light is irradiated on the light transparent container to acquire scattered light, transmitted light, and the like (see e.g., Japanese Laid-Open Patent Publication No. 2002-196007).

In the blood coagulation analyzer disclosed in Japanese Laid-Open Patent Publication No. 2002-196007, a first light source and a second light source that emit light of different wavelengths from each other, and a light detector for detecting the light from the first light source or the second light source are arranged in an accommodating section for accommodating the light transparent container. The light transparent container is configured so as to be movable between a first container position and a second container position in the accommodating section. In the blood coagulation analyzer disclosed in Japanese Laid-Open Patent Publication No. 2002-196007, the light from the first light source is detected at the first container position, and the light from the second light source is detected at the second container position, so that measurement of a plurality of analysis items can be performed with one detector.

However, the apparatus becomes more complex and also becomes larger since a mechanism for changing the position of the light transparent container in the accommodating section must be arranged in the blood coagulation analyzer disclosed in Japanese Laid-Open Patent Publication No. 2002-196007.

SUMMARY OF THE INVENTION

The scope of the present invention is defined solely by the appended claims, and is not affected to any degree by the statements within this summary. A first blood coagulation analyzer embodying features of the present invention includes: a measurement section for measuring a measurement specimen in a reaction container, the measurement specimen being a mixture of a blood specimen and a reagent; and an analyzing section for analyzing a measurement result of the measurement section; wherein the measurement section comprises: a holding section for holding the reaction container; a light emitting section for emitting light of a plurality of wavelengths towards the reaction container held by the holding section, the wavelengths comprising a first wavelength for use in a measurement performed according to a blood coagulation time method, and at least one of a second wavelength for use in a measurement performed according to a synthetic substrate method and a third wavelength for use in a measurement performed according to an immunoturbidimetric method; and a light receiving section for receiving light from the measurement specimen in the reaction container irradiated with the light of the plurality of wavelengths; and wherein the analyzing section analyzes a measurement result corresponding to the light of one of the wavelengths of the light emitted by the light emitting section, and acquires an analysis result of an analysis item corresponding to the wavelength.

A second blood analyzer embodying features of the present invention includes: a measurement section for measuring a measurement specimen in a reaction container, the measurement specimen being a mixture of a blood specimen and a reagent; and an analyzing section for analyzing a measurement result of the measurement section, wherein the measurement section comprises: a holding section for holding the reaction container; a light emitting section for emitting light towards the reaction container held by the holding section; an optical extracting section for extracting a plurality of lights comprising different wavelengths from each other from the light from the measurement specimen in the reaction container; and a light receiving section for receiving the light extracted by the optical extracting section, wherein the analyzing section analyzes a measurement result of the measurement section corresponding to the light of one wavelength of the plurality of wavelengths, and acquires an analysis result of an analysis item corresponding to the light of the wavelength.

A first blood analyzing method embodying features of the present invention includes: (a) preparing a measurement specimen by dispensing a blood specimen and a reagent into a reaction container; (b) emitting light of a plurality of wavelengths to the measurement specimen in the reaction container, the wavelengths comprising a first wavelength for use in a measurement by a blood coagulation time method, and at least one of a second wavelength for use in a measurement by a synthetic substrate method and a third wavelength for use in a measurement by an immunoturbidimetric method; (c) detecting light of a plurality of wavelengths corresponding to the light emitted in (b), from the measurement specimen, by a light receiving element, and acquiring data corresponding to each wavelength; and (d) conducting an analysis based on the data corresponding to one of the wavelengths among the acquired data, and acquiring a result of the analysis.

DETAILED DESCRIPTION OF THE PREFERRED EMBODIMENTS

The embodiments embodying the present invention will now be described based on the drawings.

First Embodiment

Figure 1:
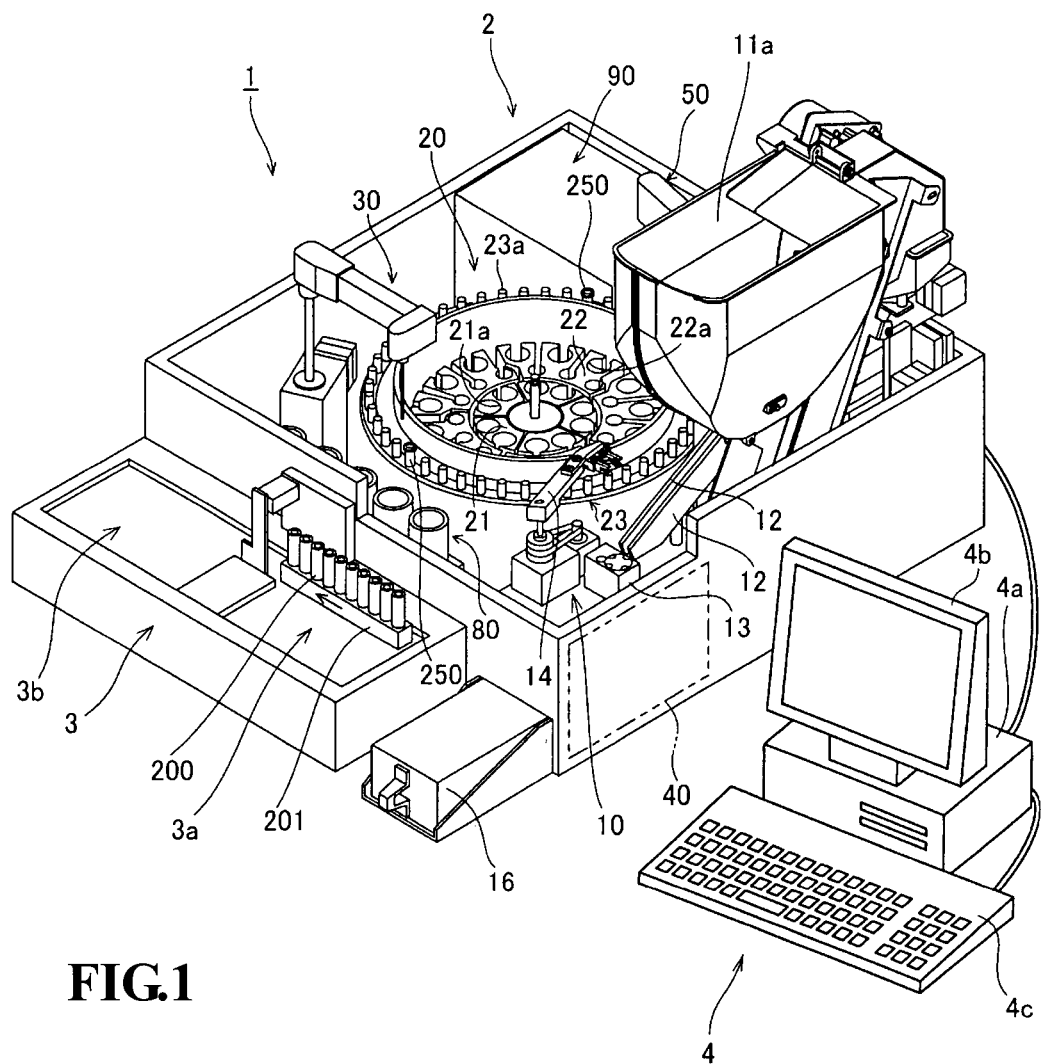
FIG. 1 is a perspective view showing an entire configuration of a blood coagulation analyzer according to a first embodiment of the present invention.
Figure 2:
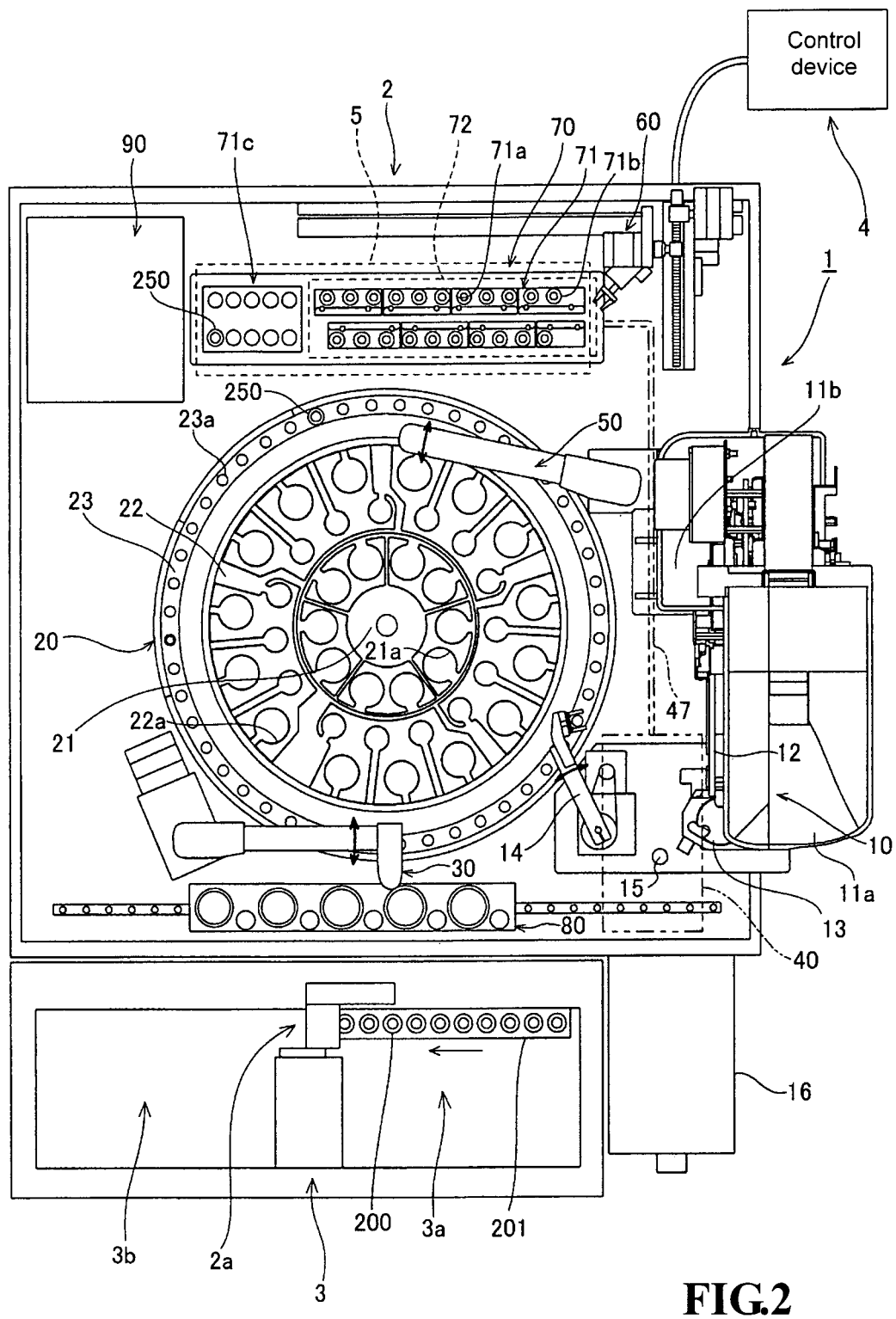
FIG. 2 is a plan view of the blood coagulation analyzer shown in FIG. 1.

FIGS. 1 and 2 are perspective view and plan view, respectively, showing the entire configuration of a blood coagulation analyzer according to a first embodiment of the present invention. FIGS. 3 to 15 are views describing the configuration of the blood coagulation analyzer according to the first embodiment shown in FIG. 1. The entire configuration of the blood coagulation analyzer 1 according to the first embodiment of the present invention will first be described with reference to FIGS. 1 to 15.

The blood coagulation analyzer 1 according to the first embodiment of the present invention is an apparatus for optically measuring and analyzing the amount of a specific substance and extent of activity related to coagulation and fibrinolytic functions of the blood, where plasma is used for the blood specimen. In the blood coagulation analyzer 1 of the first embodiment, the coagulation time of the blood specimen is measured by performing optical measurement of the blood specimen using blood coagulation time method, synthetic substrate method, immunoturbidimetric method, and platelet agglutination method.

In the coagulation time method, the time at which fibrinogen transforms to fibrin is analyzed by irradiating light having a wavelength of 660 nm to the specimen, and detecting the transmitted light or the scattered light from the specimen with the light detector. The measurement items of the coagulation time method include PT (prothrombin time), APTT (activated partial thromboplastin time), Fbg (Fibrinogen content), and the like. In the synthetic substrate method, light having a wavelength of 405 nm is irradiated on the specimen, and the transmitted light from the specimen is detected by the light detector. The measurement items of the synthetic substrate method include ATIII, α2-PI (α2-plasmin inhibitor), PLG (plasminogen) and the like. In the immunoturbidimetric method, the light having a wavelength of 800 nm is irradiated on the specimen, and the scattered light or the transmitted light from the specimen is detected by the light detector. The measurement items of the immunoturbidimetric method include D dimer, FDP, and the like. In the platelet agglutination method, light having a wavelength of 575 nm is irradiated on the specimen, and the transmitted light or the scattered light from the specimen are detected by the light detector.

The blood coagulation analyzer 1 is configured by a detection mechanism unit 2, a conveyance mechanism unit 3 arranged on the front surface side of the detection mechanism unit 2, and a control device 4 electrically connected to the detection mechanism unit 2, as shown in FIGS. 1 and 2. The detection mechanism unit 2 and the conveyance mechanism unit 3 are controlled by a control substrate 5 (see FIG. 2) arranged in the detection mechanism unit 2.

The conveyance mechanism unit 3 is adapted to convey a rack 201 mounted with a plurality of (ten in the first embodiment) test tubes 200 accommodating the blood specimen to a suction position 2a (see FIG. 2) of the detection mechanism unit 2 to supply the blood specimen to the detection mechanism unit 2. The conveyance mechanism unit 3 includes a rack set region 3a for setting the rack 201 in which the test tubes 200 accommodating non-processed blood specimen are accommodated, and a rack accommodating region 3b for accommodating the rack 201 in which the test tubes 200 accommodating processed blood specimen are accommodated.

The detection mechanism unit 2 is configured to perform optical measurement on the blood specimen supplied from the conveyance mechanism unit 3 to acquire optical information related to the supplied blood specimen. In the first embodiment, optical measurement is performed on the blood specimen dispensed into a cuvette 250 (see FIG. 9) of the detection mechanism unit 2 from the test tube 200 mounted on the rack 201 of the conveyance mechanism unit 3. The detection mechanism unit 2 includes a cuvette supply mechanism section 10, a rotation conveyance section 20, a specimen dispensing arm 30, a lamp unit 40, a reagent dispensing arm 50, a cuvette transporting section 60, a measurement section 70, an emergency specimen set section 80, and a fluid section 90, as shown in FIGS. 1 and 2.

The cuvette supply mechanism section 10 is configured to sequentially supply the plurality of cuvettes 250 randomly placed by the user to the rotation conveyance section 20. The cuvette supply mechanism section 10 includes a first hopper 11a; a second hopper 11b supplied with the cuvette 250 from the first hopper 11a and being smaller than the first hopper 11a; two induction plates 12 supplied with the cuvette 250 from the second hopper 11b; a supporting table 13 arranged on the lower end of the two induction plates 12; and a supply catcher part 14 arranged at a predetermined distance from the supporting table 13, as shown in FIGS. 1 and 2. The cuvette 250 supplied to the first hopper 11a is configured so as to slidably move towards the supporting table 13 on the induction plates 12 by way of the second hopper 11b which is smaller than the first hopper 11a. The supporting table 13 is adapted to rotatably transport the cuvette 250 slidably moved on the induction plates 12 to a position enabling the supply catcher part 14 to grip the cuvette 250. The supply catcher section 14 is arranged to supply the cuvette 250 rotatably transported by the supporting table 13 to the rotation conveyance section 20.

As shown in FIG. 2, a discarding hole 15 for discarding the cuvette 250 and a discarding box 16 arranged under the discarding hole 15 are arranged at a predetermined spacing from the supply catcher part 14 described above in the detection mechanism unit 2. The supply catcher part 14 can discard the cuvette 250 on a cuvette conveying table 23 of the rotation conveyance section 20 to the discarding box 16 through the discarding hole 15. That is, the supply catcher part 14 performs both supply and discard of the cuvette 250.

The rotation conveyance section 20 is arranged to convey the cuvette 250 supplied from the cuvette supply mechanism section 10 and a reagent container (not shown) accommodating the reagent for coagulating the blood specimen in the rotating direction. The rotation conveyance section 20 is configured by a circular reagent table 21, a circular ring shaped reagent table 22 arranged on the outer side of the circular reagent table 21, and a circular ring shaped cuvette conveying table 23 arranged on the outer side of the circular ring shaped reagent table 22, as shown in FIG. 2. The cuvette conveying table 23, the reagent table 21, and the reagent table 22 are respectively configured so as to be rotatable in both clockwise direction and counterclockwise direction and so that each table is rotatable independent from each other.

As shown in FIG. 2, the reagent tables 21 and 22 each has a plurality of holes 21a, 22a formed at a predetermined spacing along the circumferential direction. The holes 21a, 22a of the reagent tables 21 and 22 are formed to mount a plurality of reagent containers (not shown) accommodating the reagent for coagulating the blood. The cuvette conveying table 23 includes a plurality of cylindrical holding sections 23a arranged at a predetermined spacing along the circumferential direction. The holding sections 23a are arranged to hold the cuvettes 250 supplied from the cuvette supply mechanism section 10. The blood specimen accommodated in the test tube 200 stored in the rack 201, which is mounted on the conveyance mechanism unit 3, is dispensed into the cuvette 250 held at the holding section 23a of the cuvette conveyance table 23 by the specimen dispensing arm 30.

The specimen dispensing arm 30 is adapted to suction the blood specimen accommodated in the test tube 200 conveyed to the suction position 2a by the conveyance mechanism unit 3, and dispense the suctioned blood specimen into the cuvette 250 transported to the rotation conveyance section 20.

The lamp unit 40 is arranged to apply light used for optical measurement performed in the measurement section 70, as shown in FIG. 2. The lamp unit 40 is configured by a halogen lamp 41 serving as a light source, light collecting lenses 42a to 42c, a disc shaped filter part 43, a motor 44, a light transmission sensor 45, an optical fiber coupler 46, and twenty-one branched optical fibers 47 (see FIG. 5), as shown in FIGS. 4 and 5.

Figure 4:
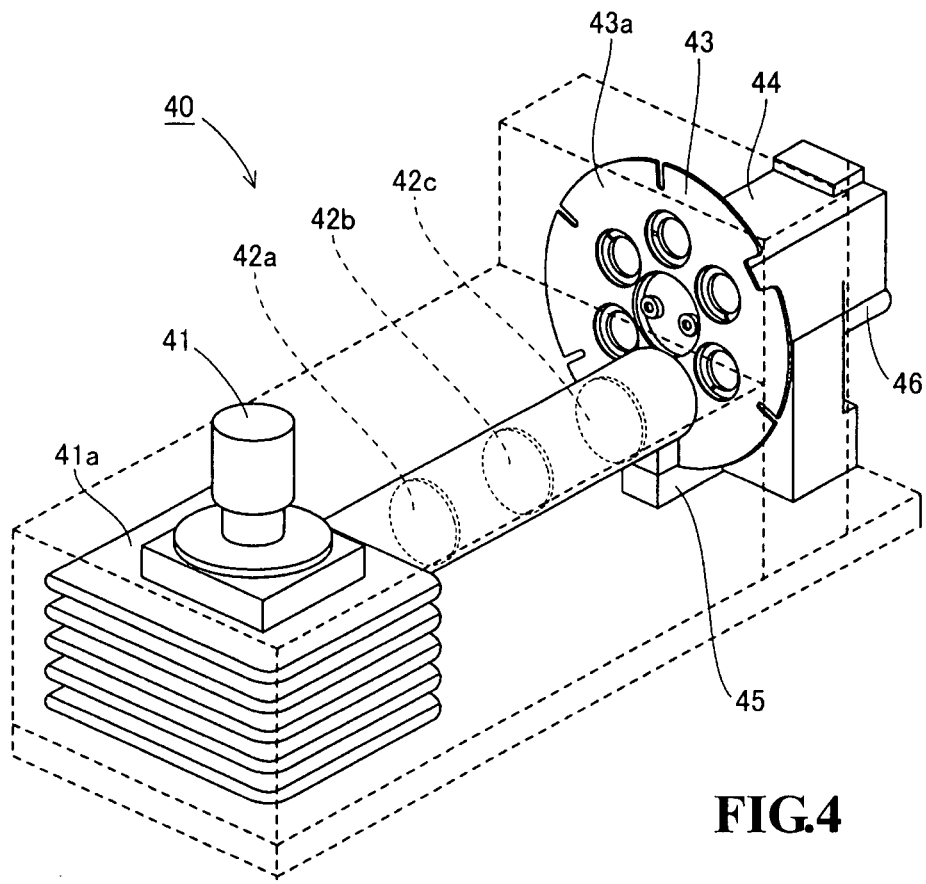
FIG. 4 is a perspective view showing a lamp unit of the blood coagulation analyzer according to the first embodiment.
Figure 5:
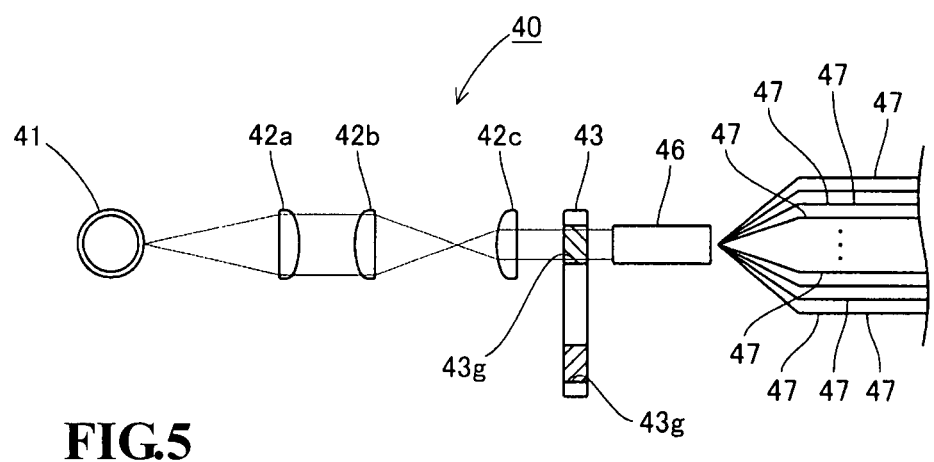
FIG. 5 is a frame format view describing the configuration of the lamp unit of the blood coagulation analyzer according to the first embodiment.

The halogen lamp 41 is accommodated in a lamp case 41a including a plurality of fins for cooling air heated by heat generation of the halogen lamp 41, as shown in FIG. 4. The light collecting lenses 42a to 42c are adapted to collect light emitted from the halogen lamp 41. The light collecting lenses 42a to 42c are arranged on an optical path for guiding the light emitted from the halogen lamp 41 towards the optical fiber coupler 46. The light emitted from the halogen lamp 41 and collected by the light collecting lenses 42a to 42c is guided to the optical fiber coupler 46 through one of the optical filters 43b to 43f of the filter part 43 to be hereinafter described.

Figure 6:
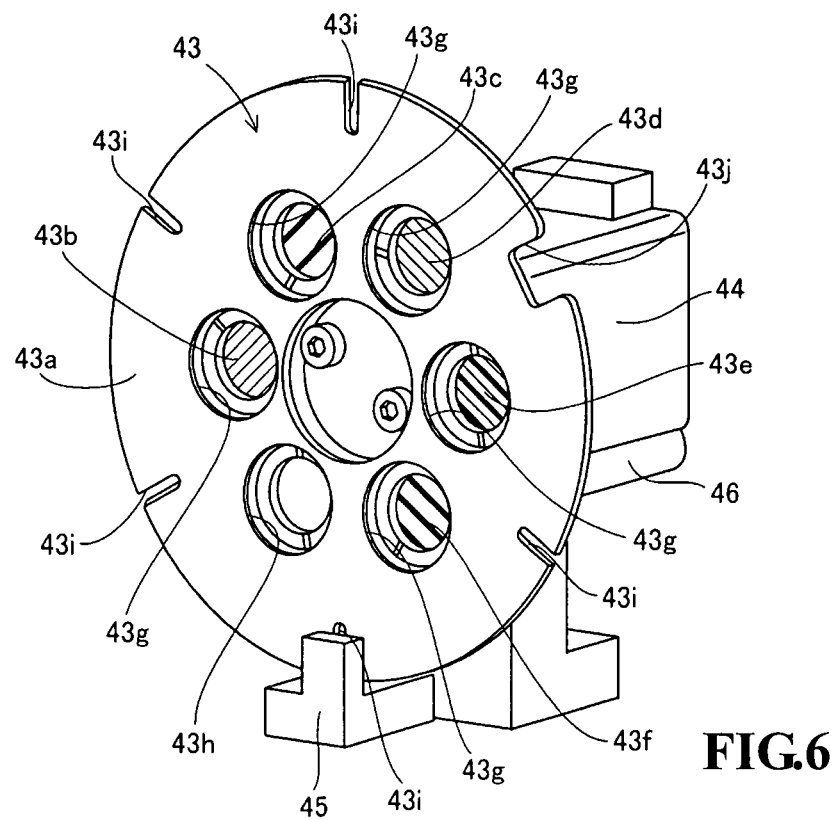
FIG. 6 is an enlarged perspective view showing a filter part of the lamp unit shown in FIG. 4.
Figure 7:
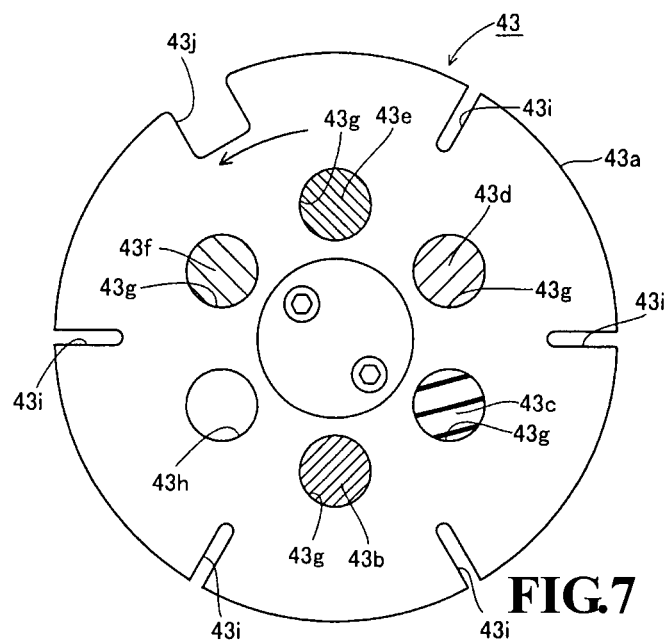
FIG. 7 is a front view showing the filter part of the lamp unit shown in FIG. 4.

As shown in FIG. 4, the filter part 43 of the lamp unit 40 is rotatably attached with a motor shaft (not shown) of the motor 44 as the center. Thus, the filter part 43 rotates with the shaft as the center by the drive of the motor 44. The filter part 43 includes a filter plate 43a arranged with five optical filters 43b to 43f having different light transmission characteristics (transparent wavelength), as shown in FIGS. 6 and 7. Five holes 43g for attaching the optical filters 43b to 43f and a hole 43h that is blocked so as not to transmit the light are formed in the filter plate 43a. The five optical filters 43b, 43c, 43d, 43e, and 43f having different light transmission characteristics (transparent wavelength) are respectively arranged in the five holes 43g. The holes 43g and 43h are formed at a predetermined angular spacing (equally spaced at 60° in the first embodiment) along the rotating direction of the filter part 43. The hole 43*h* is a spare hole, and a filter is attached thereto when additional filter becomes necessary.

The optical filters 43*b*, 43*c*, 43*d*, 43*e*, and 43*f* respectively transmit light of wavelength 340 nm, 405 nm, 575 nm, 660 nm, and 800 nm, and does not transmit light of other wavelengths. Therefore, the light that has passed through the optical filters 43*b*, 43*c*, 43*d*, 43*e*, and 43*f* have wavelength characteristic of 340 nm, 405 nm, 575 nm, 660 nm, and 800 nm.

As shown in FIG. 7, the filter plate 43*a* is formed with six slits at a predetermined angular spacing (equally spaced at 60° in the first embodiment) along the circumferential direction. One of the six slits is an origin slit 43*j* having a slit width in the rotating direction of the filter plate 43*a* larger than the other five normal slits 43*i*. The origin slit 43*j* and the normal slits 43*i* are formed at a predetermined angular spacing (equally spaced at 60° in the first embodiment) at an intermediate angle position between the adjacent holes 43*g* and 43*h*.

When light is irradiated on the cuvette 250 of a cuvette mounting part 71, to be hereinafter described, from the lamp unit 40, the drive of the motor 44 is controlled by a control substrate 5 so that the filter part 43 rotates at substantially constant speed. Therefore, with the rotation of the filter plate 43*a*, five optical filters 43*b* to 43*f* having different light transmission characteristics and one light shielded hole 43*h* (see FIG. 5) are intermittently arranged in order on the optical path of the light collected by the light collecting lenses 42*a* to 42*c* (see FIG. 4). Thus, five types of light having different wavelength characteristics are intermittently irradiated in order. In the first embodiment, the filter part 43 is configured to rotate once in 0.1 second. Therefore, five types of light having different wavelength characteristics are sequentially irradiated in a time sharing manner in 0.1 second to the cuvette 250 of the cuvette mounting part 71 to be hereinafter described. In the measurement section 70, five electrical signals corresponding to the five types of wavelength are acquired in 0.1 second by a photoelectric conversion element 72*b* (reference light photoelectric conversion element 72*e*).

The light transmission sensor 45 is arranged to detect the passing of the origin slit 43*j* and the normal slits 43*i* involved in the rotation of the filter part 43, as shown in FIG. 6. In the sensor 45, a light receiving section detects the light from the light source via the slit when the origin slit 43*j* and the normal slits 43*i* pass, and the detection signal is output. Since the origin slit 43*j* has a larger slit width than the normal slits 43*i*, the detection signal output from the sensor 45 when the origin slit 43*j* passes has a longer output period than the detection signal of when the normal slit 43*i* passes. Therefore, whether or not the filter part 43 is rotating properly can be monitored based on the detection signal from the sensor 45.

Figure 8:
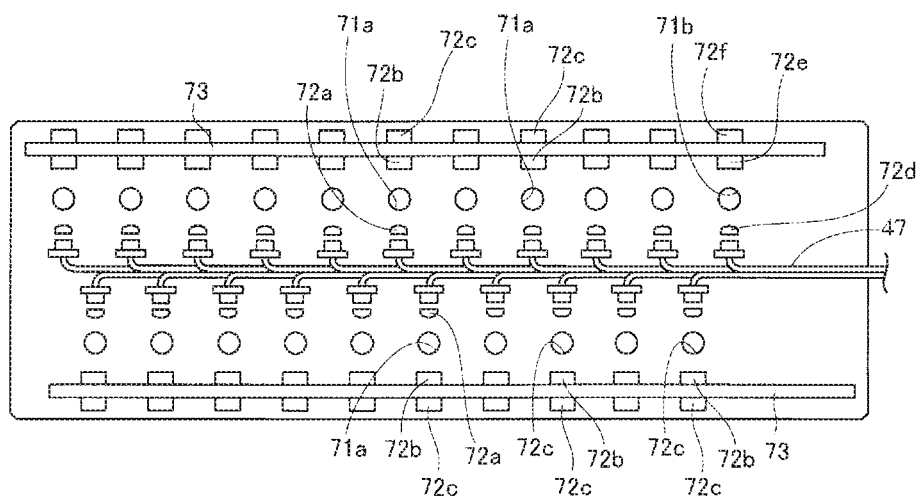
FIG. 8 is a schematic view describing an internal configuration of a detecting part of a measurement section of the blood coagulation analyzer according to the first embodiment shown in FIG. 1.
Figure 9:
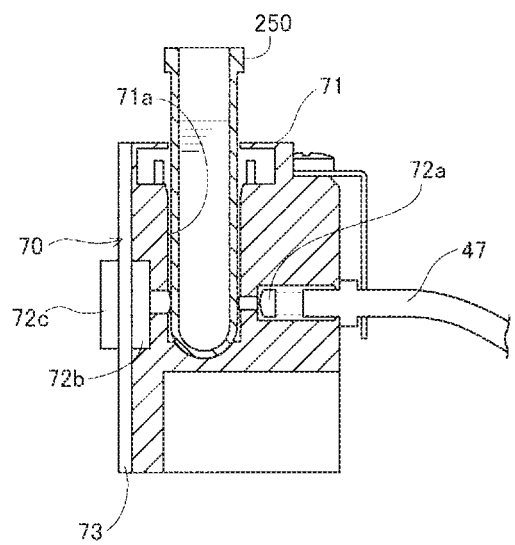
FIG. 9 is a cross sectional view describing the configuration of the detecting part of the measurement section of the blood coagulation analyzer according to the first embodiment shown in FIG. 1.

The optical fiber coupler 46 is adapted to enter the light that has passed the optical filers 43*b* to 43*f* to the twenty-one branched optical fibers 47. That is, the optical fiber coupler 46 guides the light of the same quality simultaneously to the twenty-one branched optical fibers 47. The tips of the twenty-one branched optical fibers 47 are connected to the measurement section 70, as shown in FIG. 2, so that the light from the lamp unit 40 is guided to the measurement specimen in the cuvette 250 set in the measurement section 70. Specifically, as shown in FIGS. 8 and 9, the twenty-one branched optical fibers 47 are respectively arranged to apply light to the held cuvette 250 from the side surface of the twenty insertion holes 71*a* and one reference light measurement hole 71*b* of the measurement section 70 as hereinafter described. Therefore, the five types of light having different wavelength characteristics that intermittently pass through the optical filters 43*b* to 43*f* are respectively applied to the measurement section 70 via the branched optical fibers 47.

As shown in FIGS. 1 and 2, the reagent dispensing arm 50 is arranged to mix reagent to the blood specimen in the cuvette 250 by dispensing the reagent in the reagent container (not shown) mounted on the rotation conveyance section 20 into the cuvette 250 held by the rotation conveyance section 20. The measurement specimen is prepared by adding reagent to the blood specimen. The cuvette transporting section 60 is arranged to transport the cuvette 250 between the rotation conveyance section 20 and the measurement section 70.

The measurement section 70 is arranged to warm the measurement specimen prepared by mixing reagent to the blood specimen, temporally receive light from the measurement specimen irradiated with light of a plurality of wavelengths by the lamp unit 40, and acquire temporal optical information for each wavelength. Specifically, the measurement section 70 acquires amount of transmitted light for every elapsed time using five types of light (340 nm, 405 nm, 575 nm, 660 nm, and 800 nm) emitted from the lamp unit 40. The light having the wavelength of 660 nm emitted from the branched optical fibers 47 is the main wavelength used in measuring measurement items by coagulation time method such as Fbg (Fibrinogen content), (PT (prothrombin time), and APTT (activated partial thromboplastin time). The light having the wavelength of 800 nm, is the sub-wavelength used in measuring measurement items by coagulation time method such as Fbg, PT, and APTT. The measuring wavelength of ATIII, which are the measurement item of synthetic substrate method, is 405 nm, and the measuring wavelength of D dimmer and FDP, which are the measurement items of immunoturbidimetric method, is 800 nm. The measuring wavelength of the platelet agglutination method is 575 nm. Therefore, the blood coagulation analyzer 1 according to the first embodiment is configured to obtain light of a plurality of wavelengths by passing the light emitted from the halogen lamp 41 serving as one light source through the optical filters 43*b* to 43*f* of the filter part 43, and perform the measurement of various measurement items using such light.

As shown in FIG. 2, the measurement section 70 is configured by the cuvette mounting part 71, and a detecting part 72 arranged below the cuvette mounting part 71. Twenty insertion holes 71*a* to which the cuvette 250 is inserted, and one reference light measurement hole 71*b* for measuring the reference light without being inserted with cuvette 250 are formed in the cuvette mounting part 71, as shown in FIG. 9. Furthermore, a heating portion 71*c* for heating the cuvette 250 inserted into the insertion hole 71*a* to a predetermined temperature is arranged in the cuvette mounting part 71.

The reference light measurement hole 71*b* is formed to monitor the characteristics of the light emitted from the branched optical fibers 47. Specifically, the light emitted from the branched optical fibers 47 is directly received by a reference light photoelectric conversion element 72*e* of the detecting part 72, so that characteristics such as fluctuation originating from the halogen lamp 41 (see FIG. 4) of the lamp unit 40 is detected as an electrical signal. A subtraction process is then performed on the characteristics (electrical signal) of the detected light from the signal corresponding to the transmitted light of the measurement specimen in the cuvette 250 inserted in the insertion hole 71*a* to correct the signal corresponding to the transmitted light of the measurement specimen. Production of microscopic errors due to characteristics of the light for every measurement of the optical information is thereby suppressed.

Figure 10:
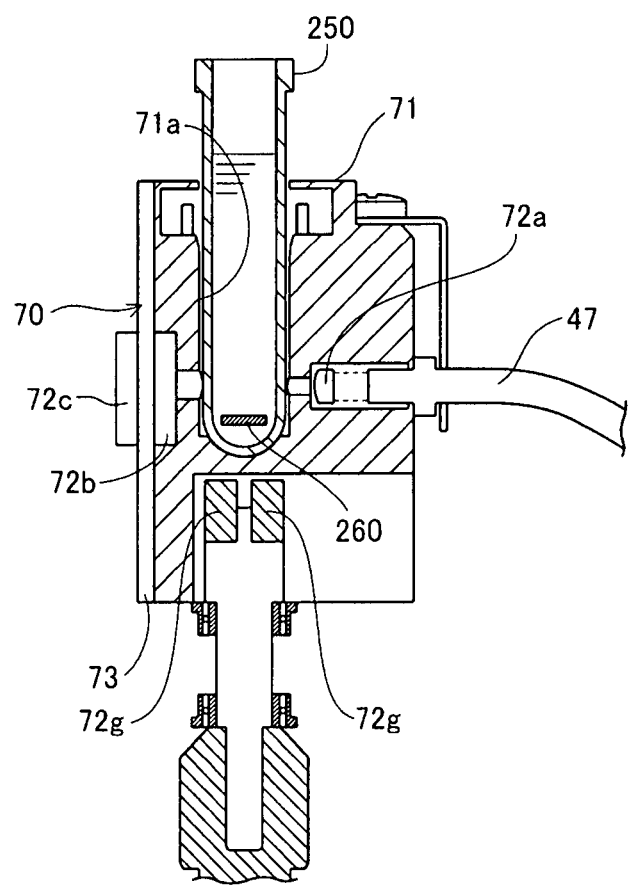
FIG. 10 is a cross sectional view corresponding to FIG. 9 when platelet agglutination measurement is performed.

The detecting part 72 of the measurement section 70 is configured to perform optical measurements under a plurality of conditions on the measurement specimen in the cuvette 250 inserted in the insertion hole 71a. As shown in FIGS. 8 and 9, a collimator lens 72a, a photoelectric conversion element 72b, and a pre-amplifier 72c are arranged in the detecting part 72 in correspondence to each insertion hole 71a inserted with the cuvette 250. As shown in FIG. 8, a reference light collimator lens 72d, a reference light photoelectric conversion elements 72e, and a reference light pre-amplifier 72f are arranged in correspondence to the reference light measurement hole 71b. Moreover, as shown in FIG. 10, a rotatable magnet 72g is arranged at the lower part of a predetermined insertion hole out of the twenty insertion holes 71a. When measuring by platelet agglutination method, a rod shaped stirrer bar 260 having magnetic property is placed in the cuvette 250 accommodating the measurement specimen. The measurement specimen can be stirred during the measurement as the stirrer bar 260 rotates with the rotation of the magnet 72g. According to such configuration, the blood coagulation analyzer 1 of the first embodiment is configured to enable measurement by platelet agglutination method.

As shown in FIG. 8, the collimator lens 72a is arranged between the ends of the branched optical fibers 47 guiding the light from the lamp unit (see FIG. 1) and the corresponding insertion hole 71a. The collimator lens 72a is arranged to collimate the light exit from the branched optical fibers 47 to parallel light. The photoelectric conversion element 72b is attached to the surface on the side of the insertion hole 71a of the substrate 73 arranged so as to face the ends of the branched optical fibers 47 with the insertion hole 71a in between. The pre-amplifier 72c is attached to the surface on the side opposite to the insertion hole 71a of the substrate 73. The photoelectric conversion element 72b is adapted to detect the light (hereinafter referred to as transmitted light) that has transmitted the measurement specimen when light is irradiated on the measurement specimen in the cuvette 250 inserted in the insertion hole 71a, and to output the electrical signal (analog signal) corresponding to the detected transmitted light. The pre-amplifier 72c of the detecting part 72 is arranged to amplify the electrical signal (analog signal) from the photoelectric conversion element 72b.

The reference light collimator lens 72d, the reference light photoelectric conversion element 72e, and the reference light pre-amplifier 72f arranged in the detecting part 72 in correspondence to the reference light measurement hole 71b are configured similar to the collimator lens 72a, the photoelectric conversion element 72b, and the pre-amplifier 72c arranged in the detecting part 72 in correspondence to the insertion hole 71a. The reference light photoelectric conversion element 72e is configured such that after the light exit from the branched optical fibers 47 is transmitted through the reference light collimator lens 72d as reference light, the light directly enters the reference light photoelectric conversion element 72e. That is, the reference light photoelectric conversion element 72e is configured to detect the reference light emitted without passing through the cuvette 250 accommodating the measurement specimen, and outputting the electrical signal (analog signal) corresponding to the detected reference light.

Figure 11:
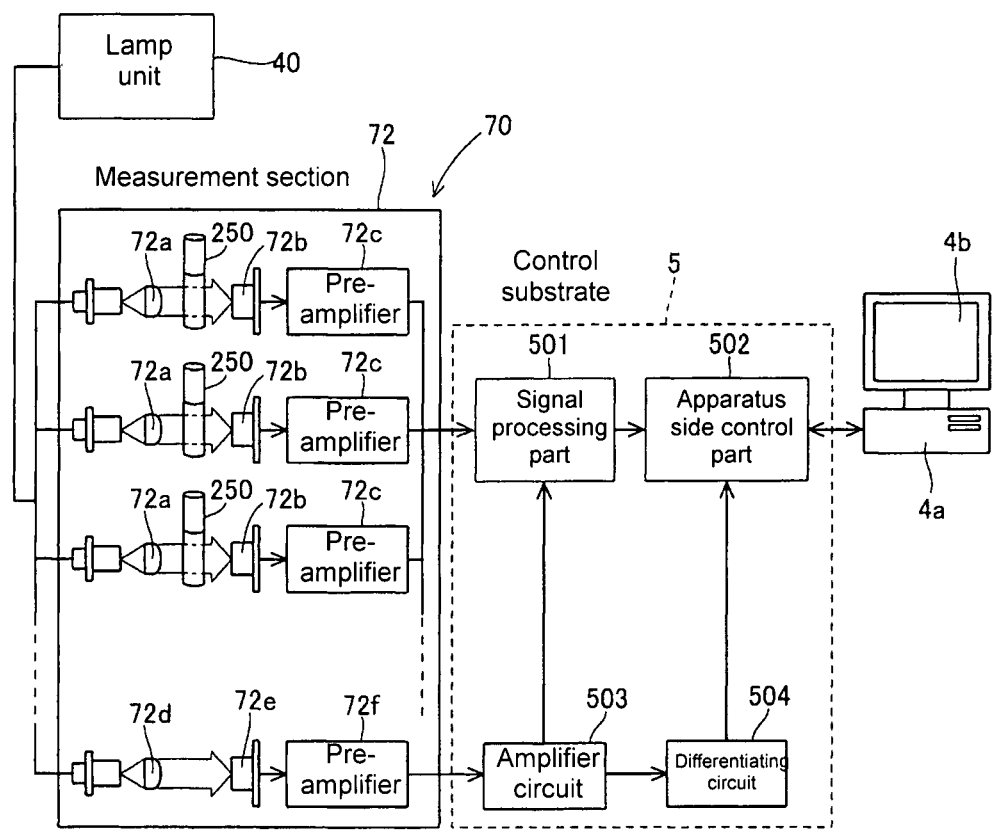
FIG. 11 is a block diagram describing the configuration of the measurement section of the blood coagulation analyzer according to the first embodiment shown in FIG. 1.
Figure 12:
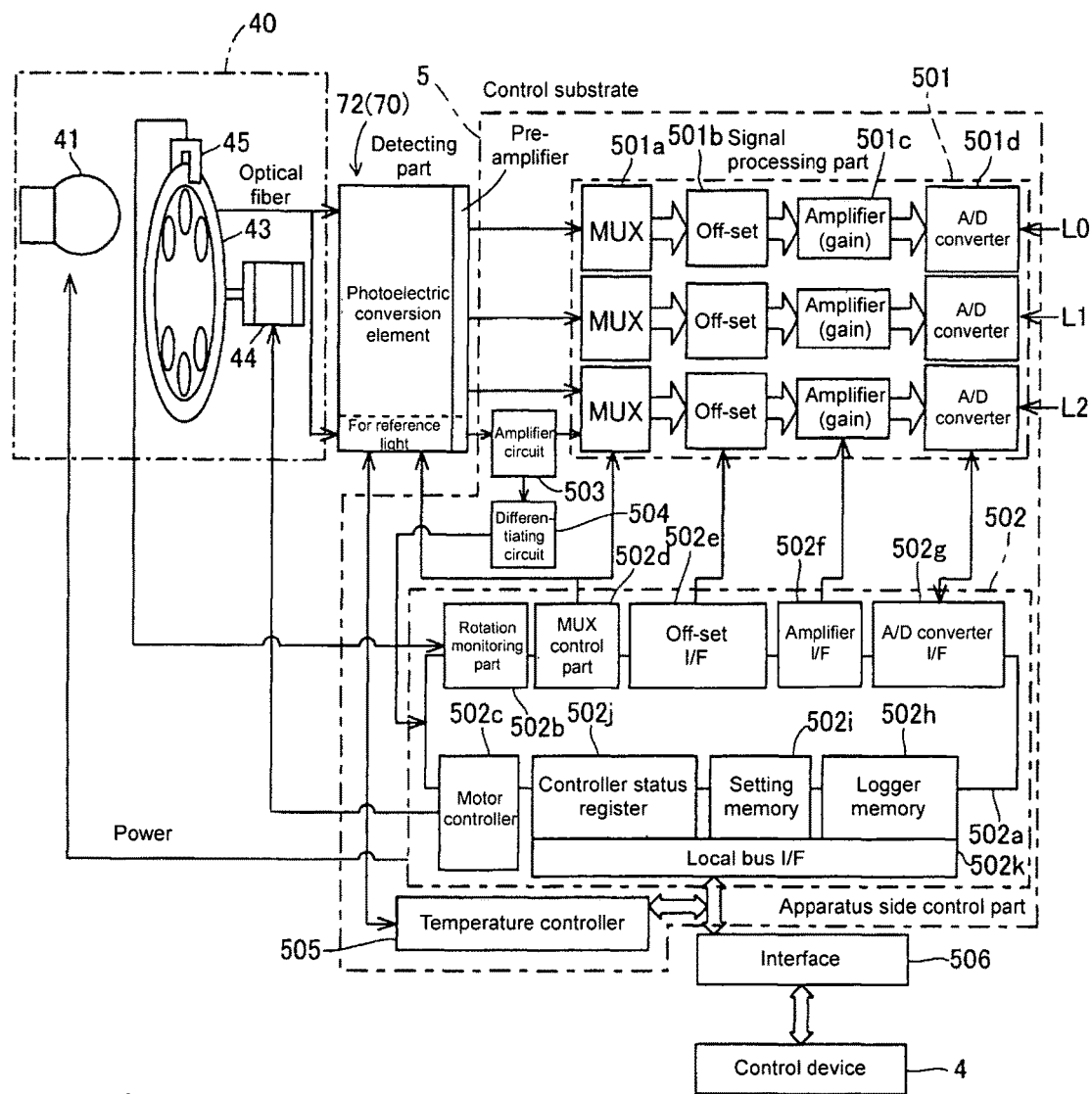
FIG. 12 is a block diagram describing components of the measurement section and the control substrate of the blood coagulation analyzer according to the first embodiment shown in FIG. 1.

The control substrate 5 is arranged below the measurement section 70. The control substrate 5 is adapted to control the operation of the detection mechanism unit 2, conveyance mechanism unit 3, and the like, and process and store the optical information (electrical signal) output from the measurement section 70. As shown in FIGS. 11 and 12, the control substrate 5 is arranged with a signal processing part 501, an apparatus side control part 502, an amplifier circuit 503, a differentiating circuit 504, and a temperature controller 505 (see FIG. 12). The signal processing part 501 is arranged to perform processes on the signal output by detecting the transmitted light by the photoelectric conversion element 72b when light is irradiated on the measurement specimen from the lamp unit. The signal processing part 501 includes three multiplexers (MUX) 501a, three offset circuits 501b, three amplifiers 501c, and three A/D converters 501d, as shown in FIG. 12. One of each of the multiplexer 501a, the offset circuit 501b, the amplifier 501c, and the A/D converter 501 configure one signal processing line L0. In addition to the signal processing line L0, signal processing lines L1 and L2 having the configuration similar to the signal processing lien L0 are arranged in the signal processing part 501. That is, three signal processing lines L0 to L2 for processing a plurality of analog signals output from the detecting part 72 are arranged in the signal processing part 501.

Figure 13:
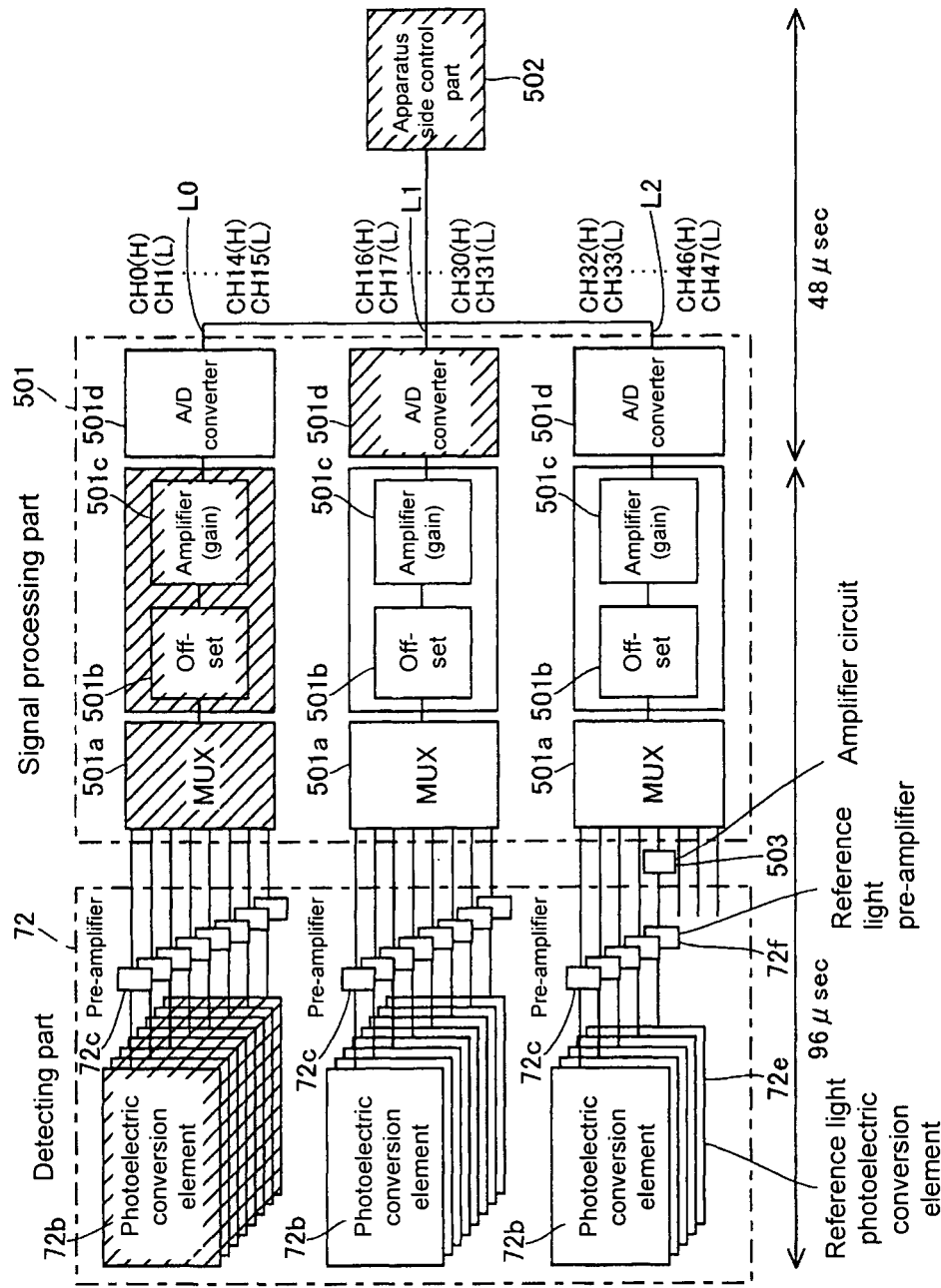
FIG. 13 is a block diagram describing the configuration of the detecting part and the signal processing part of the blood coagulation analyzer according to the first embodiment shown in FIG. 1.

As shown in FIG. 13, the multiplexer 501a is connected to a plurality of pre-amplifiers 72c (reference light pre-amplifier 72f). The multiplexer 501a is configured to select the analog signal one at a time from the plurality of analog signals input from the plurality of photoelectric conversion elements 72b (reference light photoelectric conversion element 72e) via the pre-amplifier 72c (reference light pre-amplifier 72f), and sequentially output the signal to the offset circuit 501b. The offset circuit 501b is adapted to correct the signal output from the multiplexer 501a. Specifically, the offset circuit 501b is provided with an offset value corresponding to the insertion hole 71a or the reference light measurement hole 71b used in the measurement from the apparatus side control part 502 (see FIG. 12). The offset circuit 501b is configured to correct the signal corresponding to the transmitted light output from the multiplexer 501a by performing the process of subtracting the offset value from the signal corresponding to the transmitted light output from the multiplexer 501a.

The amplifier 501c is adapted to amplify the analog signal output from the offset circuit 501b. The gain (amplification factor) of the amplifier 501c is controlled by the apparatus side control part 502 so as to be switched between two types of L gain and H gain, which is a value higher than the L gain. The signal of L gain (amplification factor) and the signal of H gain (amplification factor) amplified by the amplifier 501c are input to the A/D converter 501d at timings different from each other. The A/D converters 501d are respectively connected to the amplifier 501c and are arranged to convert the processed analog signal amplified to signal (analog signal) of L gain and H gain by the amplifier 501c to digital signal (data).

In the first embodiment, forty-eight (sixteen for each A/D converter) data corresponding to channels CH0 to CH47 are output from the A/D converter 501d, as shown in FIG. 13. Among the channels CH0 to CH47, the data of the forty-two channels of CH0 to CH41 correspond to the data based on the electrical signal obtained from each photoelectric conversion element 72b or the reference light photoelectric conversion element 72e. That is, the twenty data obtained from the twenty photoelectric conversion elements 72b are amplified at L gain (amplification factor) and H gain (amplification factor) by the amplifier 501c of the signal processing part 501 to become forty data. One datum obtained from the one reference light photoelectric conversion element 72e is amplified at L gain (amplification factor) and H gain (amplification factor) by the amplifier 501c of the signal processing part 501 (see FIG. 12) to become two data. The forty-two data, which is the total of the forty data and the two data corresponding to the reference light, correspond to the data of channels CH0 to CH41. The remaining six channels CH42 to CH47 of the channels CH0 to CH47 are spare channels that are not used in the first embodiment, and the data of the channels CH42 to CH47 do not correspond to the electrical signal from the photoelectric conversion element 72b or the reference light photoelectric conversion element 72e.

The apparatus side control part 502 is adapted to control the operation of the detection mechanism unit 2 and the conveyance mechanism unit 3, and is adapted to acquire and store digital signal (data) output from the A/D converter 501d. The apparatus side control part 502 includes controller 502a, filter part rotation monitoring part 502b, motor controller 502c, multiplexer controlling part 502d, offset interface 502e, amplifier interface 502f, A/D converter interface 502g, logger memory 502h, setting memory 502i, controller status register 502j, and local bus interface 502k, as shown in FIG. 12.

The controller 502a has a function of overall controlling various controls by the apparatus side control part 502. The filter part rotation monitoring part 502b is arranged to monitor whether or not the filter part 43 of the lamp unit 40 is rotating properly. The detection signal from the sensor 45 for detecting the passing of the origin slit 43j (see FIG. 7) or the normal slit 43i involved in the rotation of the filter part 43 is input to the filter part rotation monitoring part 502b. The filter part rotation monitoring part 502b monitors whether or not the filter part 43 is rotating properly by monitoring the time interval in which the detection signal of the origin slit 43j (see FIG. 7) is output from the sensor 45, the time interval in which the detection signal of the normal slit 43i (see FIG. 7) is output from the sensor 45, and the number of times the detection signal of the normal slit 43i is output from when the detection signal of the origin slit 43j is output from the sensor 45 until the detection signal of the origin slit 43j is again output. The motor controller 502c is adapted to control the rotation number of the motor 44 for rotating the filter part 43. The multiplexer controlling part 502d is adapted to control the operation of the multiplexer 501a. Specifically, the multiplexer controlling part 502d controls the operation of the multiplexers 501a so that the time at which the plurality of multiplexers 501a selects the analog signal differs from one another.

As shown in FIG. 12, the controller 502a is configured to control the operation of the offset circuit 501b, the amplifier 501c, and the A/D converter 501d of the signal processing part 501 via the offset interface 502e, the amplifier interface 502f, and the A/D converter interface 502g. Specifically, the controller 502a supplies a predetermined offset value to the offset circuit 501b via the offset interface 502e and controls the offset circuit 501b to perform the correcting process by subtracting the offset value from the signal from the multiplexer 501a. The controller 502a also controls the amplifier 501c to be L gain or H gain via the amplifier interface 502f, and controls the amplifying process of the signal from the offset circuit 501b by the amplifier 501c. Furthermore, the controller 502a controls the conversion process of the signal (analog signal) from the amplifier 501c to the digital signal by the A/D converter 501d via the A/D converter interface 502g. The digital signal (data) acquired by the A/D converter 501d is configured to be input and stored in the logger memory 502h via the A/D converter interface 502g and the controller 502a. In this case, the controller 502a controls the operation of the A/D converter 501d via the A/D converter interface 502g so that the period in which the plurality of A/D converters 501d outputs the plurality of digital signals do not overlap.

The controller 502a is adapted to switch among the multiplexer 501a, the offset circuit 501b, the amplifier 501c, the A/D converter 501d, and the logger memory 502h of the respective signal lines L0 to L2 to the element that is to execute the process so that during the period in which the analog signal processing by the multiplexer 501a, the offset circuit 501b, and the amplifier 501c of the predetermined signal processing lines (one of L0 to L2) is performed, the conversion process by the A/D converter 501d of the signal processing line different from the predetermined signal processing line and the data storing process to the logger memory 502h of the apparatus side control part 502 are performed. This aspect will be described in detail in the analyzing operation to be hereinafter described.

Figure 14:
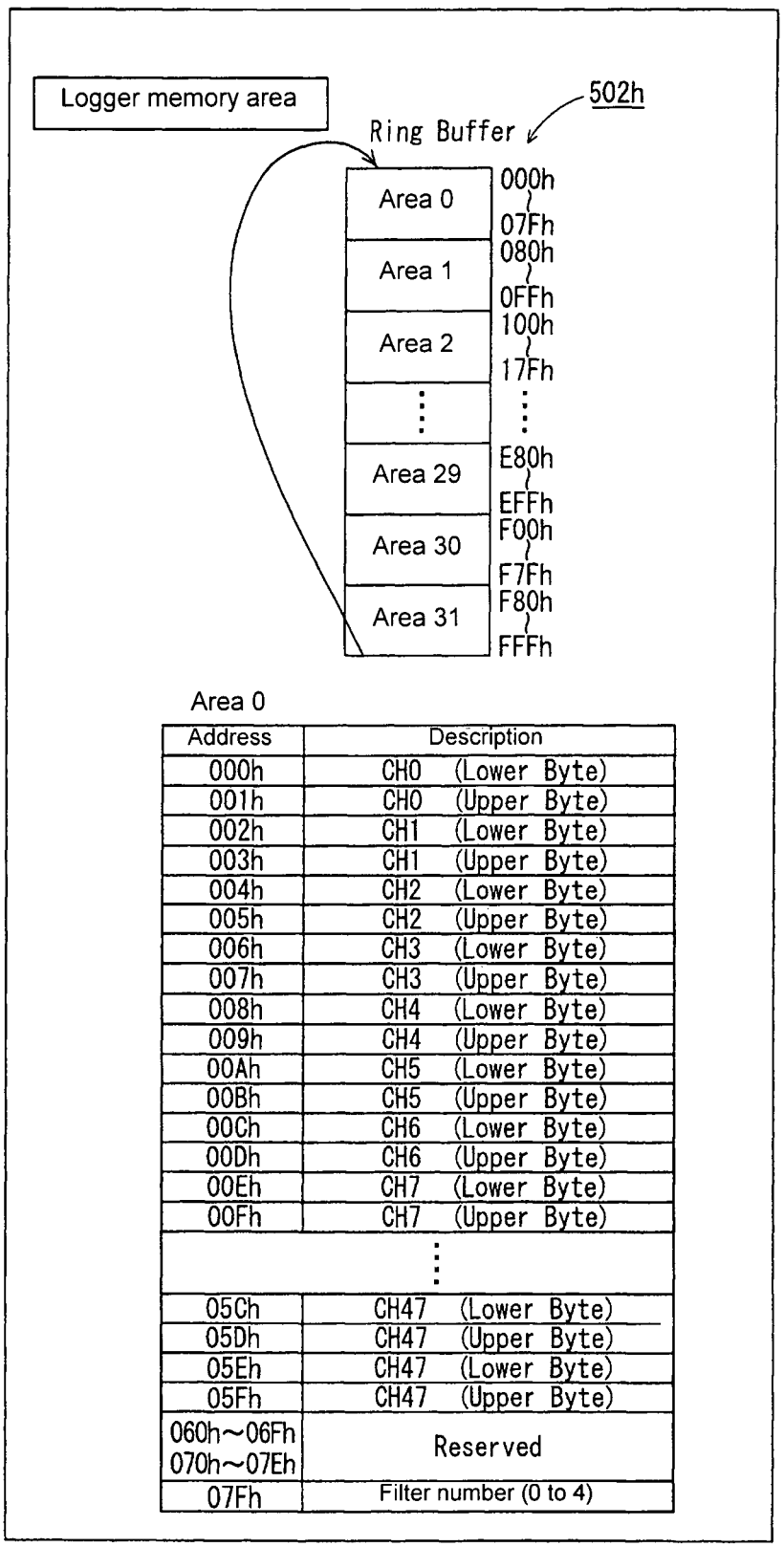
FIG. 14 is a view describing the configuration of a logger memory of a control substrate of the blood coagulation analyzer according to the first embodiment of the present invention.

The logger memory 502h is arranged to store the digital signal (data) corresponding to the analog signal output from the predetermined photoelectric conversion element 72b in a manner identifiable by the address of the logger memory 502h. The logger memory 502h is configured by thirty-two areas 0 to 31 in sections of 128 bytes, as shown in FIG. 14. Data corresponding to the transmitted light of the five optical filters 43b to 43f (see FIG. 7) and data corresponding to the blocked hole 43h are stored in the areas 0 to 31. That is, data corresponding to the transmitted light of the optical filters 43b to 43f having five different light transmission characteristics are generated every time the filter part 43 makes one rotation. The five data are stored for every area in order from area 0 of the logger memory 502h (see FIG. 14). "0" is stored as the data corresponding to the hole 43h in the sixth area. The six areas of the logger memory 502h are thus used every time the filter part 43 makes one rotation (about 100 msec), and data is overwritten again from area 0 after areas up to area 31 are used up.

Each area 0 to 31 of the logger memory 502h has 128 addresses. For example, area 0 has 128 addresses of 000g to 00Fh, 010h to 01Fh, 020h to 02Fh, 030h to 03Fh, 040h to 04Fh, 050h to 05Fh, 060h to 06Fh, and 070h to 07Fh. The data of the channels CH0 to CH47 (see FIG. 13) described above are stored in the ninety-six addresses of 000h to 05Fh. Each data of the channel CH0 to CH47 is configured to be stored in two addresses. Since data are not output from the channels CH42 to 47 in the first embodiment described above, data are not stored in the addresses corresponding to such channels.

The addresses 060h to 06Fh and 070h to 07Eh in area 0 of the logger memory 502h shown in FIG. 14 are spare addresses in which data are not stored in the first embodiment. The filter number (0 to 4) is stored in the last address 07Fh of the area 0. The filter numbers (0 to 4) are numbers for identifying the five optical filters 43b to 43f (see FIG. 7). The optical filter can be identified by detecting the timing the origin slit 43j passes. When the filter numbers (0 to 4) corresponding to the five optical filters 43b to 43f are stored in the address 07Fh, identification can be made on which data corresponding to the transmitted light of which optical filter (43b to 43f) is the data stored in the area 0.

The setting memory 502i shown in FIG. 12 is arranged to store the offset value supplied to the offset circuit 501b and the set value such as gain (amplification factor) supplied to the amplifier 501c. The controller status register 502j is arranged to temporarily store information such as whether or not the filter part 43 is rotating properly, presence or absence of conversion error from analog signal to the digital signal by the A/D converter 501d, acquiring state of data from the logger memory 502h by a control part 4a, and presence or absence of instruction to start measurement from the control part 4a. The apparatus side control part 502 is configured to adapt to transmitting data (optical information) of measurement specimen stored in the logger memory 502h to the control part 4a via the local bus interface 502k and the interface 506.

Figure 15:
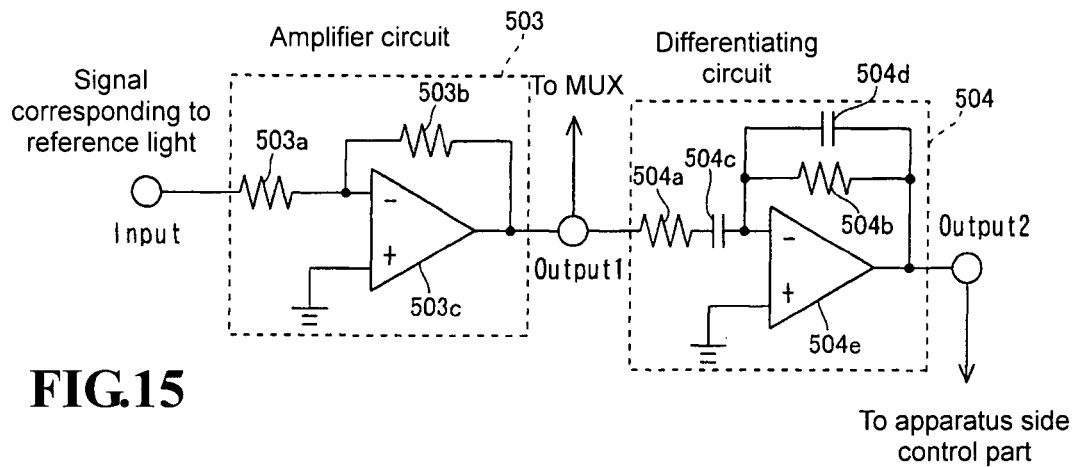
FIG. 15 is a circuit view showing a circuit configuration of an amplifier circuit and a differentiating circuit of the control substrate of the blood coagulation analyzer according to the first embodiment of the present invention.

The amplifier circuit 503 of the control substrate 5 shown in FIG. 12 is adapted to being input with the signal output from the reference light photoelectric conversion element 72e (see FIG. 13) via the reference light pre-amplifier 72f, and amplifying the input signal. The amplifier circuit 503 is configured by two resistors 503a and 503b, and one operational amplifier 503c, as shown in FIG. 15. One end of the resistor 503a is input with the signal corresponding to the reference light from the reference light pre-amplifier 72f and the other end is connected to an inverted input terminal of the operational amplifier 503c. The resistor 503b is connected between the output terminal and the inverted input terminal of the operational amplifier 503c. The non-inverted input terminal of the operational amplifier 503c is grounded. The output of the operational amplifier 503c is input to the multiplexer 501a of the signal processing part 501 (see FIG. 12) and the differentiating circuit 504.

The differentiating circuit 504 of the control substrate 5 is adapted to generate the differential signal of the signal (hereinafter referred to as reference signal) corresponding to the reference light from the amplifier circuit 503. As shown in FIG. 15, the differentiating circuit 504 is configured by two resistors 504a and 504b, two capacitors 504c and 504d, and one operational amplifier 504e. One end of the resistor 504a is input with the reference signal from the amplifier circuit 503, and the other end is connected to one of the electrodes of the capacitor 504c. The other electrode of the capacitor 504c is connected to the inverted input terminal of the operational amplifier 504e. The resistor 504b and capacitor 504d are both connected between the output terminal and the inverted input terminal of the operational amplifier 504e. The non-inverted input terminal of the operational amplifier 504e is grounded. The output of the operational amplifier 504e is input to the controller 502a of the apparatus side control part 502 (see FIG. 12) via a comparator (not shown).

The temperature controller 505 of the control substrate 5 shown in FIG. 12 is adapted to control the temperature of the heating portion 71c (see FIG. 2) of the measurement section 70. The temperature controller 505 is configured to control the temperature of the heating portion 71c of the measurement section 70 according to the set temperature (about 37° C.) input from the control part 4a via the interface 506, as shown in FIG. 12.

As shown in FIGS. 1 and 2, the emergency specimen set section 80 is arranged to perform a specimen analyzing process on the urgent blood specimen. The emergency specimen set section 80 is configured to be able to cut in the emergency specimen when the specimen analyzing process is being performed on the blood specimen supplied from the conveyance mechanism unit 3. The fluid section 90 is arranged to supply liquid such as cleaning fluid to the nozzle arranged on each dispensing arm in the shut-down process of the blood coagulation analyzer 1.

The control device 4 (see FIG. 1) consists of personal computer (PC) and the like, and includes control part 4a of CPU, ROM, RAM etc., display part 4b, and keyboard 4c. The display part 4b is arranged to display information related to interfering substances (hemoglobin, milky fluid (fat), and bilirubin) in the blood specimen, analysis result (coagulation time) obtained by analyzing the data of the digital signal transmitted from the measurement section 70, and the like.

Figure 3:
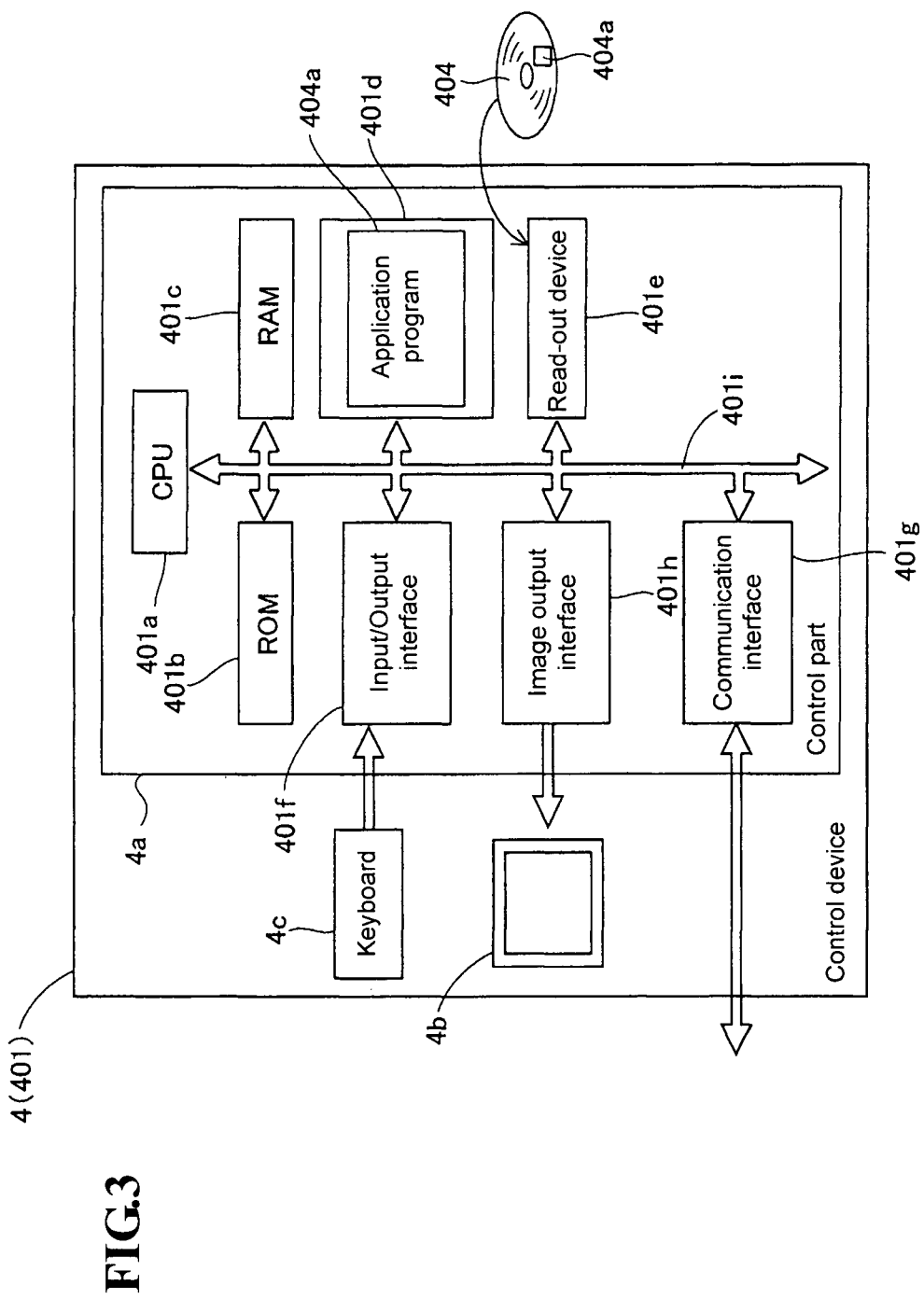
FIG. 3 is a block diagram of a control device of the blood coagulation analyzer according to the first embodiment.

The configuration of the control device 4 will now be described. As shown in FIG. 3, the control device 4 is configured by a computer 401 configured mainly by control part 4a, display part 4b, and keyboard 4c. The control part 4a is mainly configured by CPU 401a, ROM 401b, RAM 401c, hard disc 401d, read-out device 401e, input/output interface 401f, communication interface 401g, and image output interface 401h. The CPU 401a, the ROM 401b, the RAM 401c, the hard disc 401d, the read-out device 401e, the input/output interface 401f, the communication interface 401g, and the image output interface 401h are connected by bus 401i.

The CPU 401a can execute computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The application program 404a for blood coagulation time measurement according to the first embodiment is also installed in the hard disc 401d.

The read-out device 401e is configured by flexible disc drive, CD-ROM drive, DVD-ROM drive, and the like, and is able to read out computer programs and data recorded on a portable recording medium 404. The application program 404a for blood coagulation time measurement is stored in the portable recording medium 404, where the computer 401 can read out the application program 404a from the portable recording medium 404, and install the application program 404a to the hard disc 401d.

The application program 404a is not only provided by the portable recording medium 404, and may be provided through communication line (wired or wireless) from external devices communicatably connected with the computer 401 by the communication line. For instance, the application program 404a may be stored in the hard disc of the server computer on the internet, where the computer 401 can access the server computer to download the application program 404a and install the application program 404a in the hard disc 401d.

Operating system providing graphical interface environment such as Windows (registered trademark) manufactured and sold by US Microsoft Co. is installed in the hard disc 401d. In the following description, the application program 404a according to the first embodiment is assumed to be operating on the operating system.

The output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401*f*, so that the user can input data to the computer 401 using the keyboard 4*c*.

The communication interface 401*g* is, for example, Ethernet (registered trademark) interface. The computer 401 transmits and receives data with the detection mechanism unit 2 using a predetermined communication protocol by means of the communication interface 401*g*.

The image output interface 401*h* is connected to the display part 4*b* configured by LCD, CRT, or the like, and is configured to output the image signal corresponding to the image data provided from the CPU 401*a* to the display part 4*b*. The display part 4*b* displays the image (screen) according to the input image signal.

The application program 404*a* for blood coagulation time measurement installed in the hard disc 401*d* of the control part 4*a* measures the coagulation time of the measurement specimen using the amount of transmitted light (data of digital signal) of the measurement specimen transmitted from the measurement section 70 of the detection mechanism unit 2. The coagulation time is the time (coagulation time) from the point the reagent for coagulating the blood specimen in the cuvette 250 is added up to the point the measurement specimen (blood specimen added with reagent) loses fluidity. The coagulation reaction in which the measurement specimen loses fluidity is the reaction in which fibrinogen in the blood specimen transforms to fibrin by the added reagent. In the blood coagulation analyzer 1 of the first embodiment, the coagulation reaction that reacts depending on the amount of fibrinogen in the blood specimen is checked by the amount of change (difference in amount of transmitted light before reaction and amount of transmitted light after reaction) in the amount of transmitted light of the measurement specimen.

The outline of the control of the apparatus main body (detection mechanism unit 2 and conveyance mechanism unit 3) of the blood coagulation analyzer 1 by the control part 4*a* of the control device 4 will now be described with reference to FIGS. 1, 4, and 16.

The blood coagulation analyzer 1 is activated by turning ON the power of the control device 4 and the apparatus main body.

Figure 16:
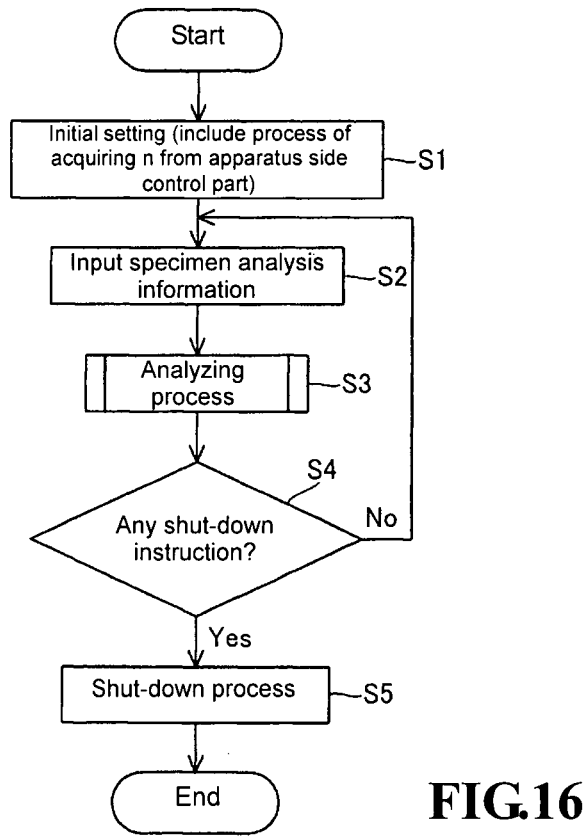
FIG. 16 is a flow chart showing the outline of a controlling method by the control part of the control device of the blood coagulation analyzer according to the first embodiment of the present invention.

When the powers are turned ON, initial setting is first performed by the PC main body 4*b* in step S1 shown in FIG. 16. In the initial setting, initialization of software stored in the control part 4*a*, process of acquiring p clock, to be hereinafter described, from the apparatus side control part 502 of the control substrate 5, and the like are performed. When the power of the apparatus main body (detection mechanism unit 2 and conveyance mechanism unit 3) is turned ON, light is emitted from the halogen lamp of the lamp unit 40 (see FIG. 4), and the filter part 32 starts to rotate at constant speed of rotation speed of 10 rotations/sec. in the initial setting of step S1. Emission of light from the halogen lamp 41 and the rotation of the filter part 43 are continued until the power of the apparatus main body (detection mechanism unit 2 and conveyance mechanism unit 3) is turned OFF. In step S2, process of accepting input of specimen analysis information by the user is performed. That is, the user inputs information in the columns of specimen number and measurement item in the specimen analysis list output to the display part 4*b* using the keyboard 4*c* of the control device 4 (see FIG. 1). The specimen analysis information is saved in the control part 4*a*.

In step S3, analyzing process is instructed by the control part 4*a*. The analyzing process is thereby performed by the apparatus main body (detection mechanism unit 2 and conveyance mechanism unit 3). Subsequently, in step S4, judgment is made whether or not instruction of shut-down of the blood coagulation analyzer 1 is input by the control part 4*a*. If judged that instruction of shut-down of the blood coagulation analyzer 1 is not input by the control part 4*a* in step S4, the process returns to step S2, and process of accepting the input of other specimen analysis information by the user is performed. If judged that instruction of shut-down of the blood coagulation analyzer 1 is input by the control part 4*a* in step S4, on the other hand, the shut-down process is performed in step S5. The power of the blood coagulation analyzer 1 is automatically turned OFF by the shut-down process, and the operation of the blood coagulation analyzer 1 is terminated.

A method of the calculation process of p clock by the apparatus side control part 502 of the control substrate 5 will now be described in detail with reference to FIGS. 4, 8, 11, 12, 17, and 18.

Figure 17:
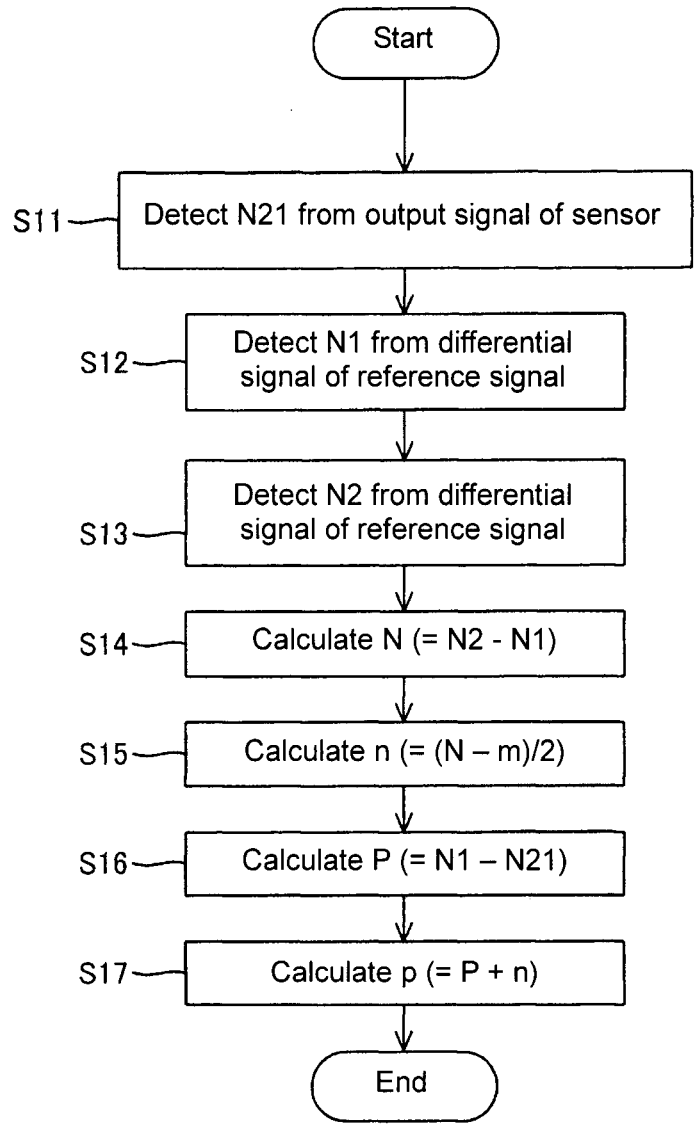
FIG. 17 is a flow chart showing the calculation process of p clock by the apparatus side control part in the initial setting shown in step S1 of FIG. 16.
Figure 18:
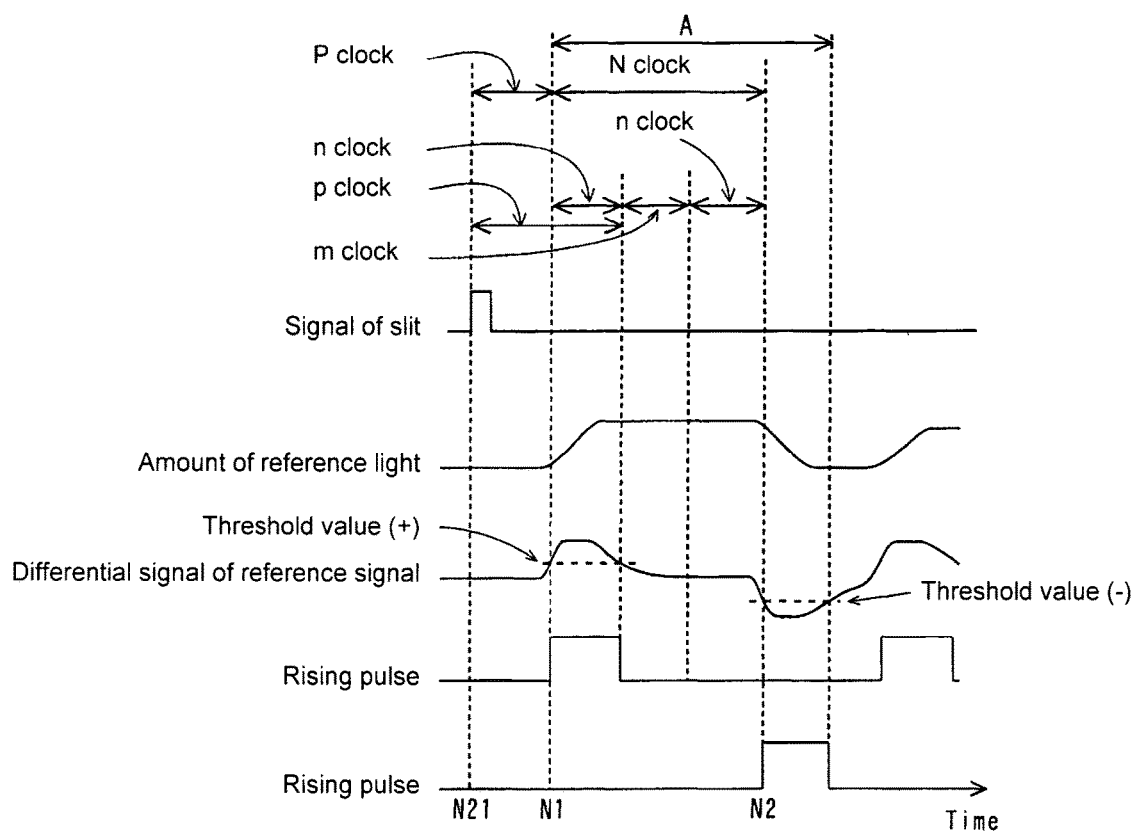
FIG. 18 is a waveform chart showing the slit detection signal, as well as the change in amount of reference light and differential signal of the reference signal used in the calculation process method of the p clock shown in FIG. 17.

First, in step S11 of FIG. 17, number of clocks N21 at the point the sensor 45 detects the slit is detected based on the signal from the sensor 45 by the apparatus side control part 502 while the filter part 43 is rotating. As shown in FIG. 18, the amount of reference light entered from the lamp unit 40 to the reference light photoelectric conversion element 72*e* (see FIG. 8) while the filter part 43 (see FIG. 4) is rotating at a constant speed changes in a waveform indicated as "amount of reference light". The period A in FIG. 18 is the period in which one of the optical filters 43*b* to 43*f* of the rotating filter part 43 is arranged in the optical path of the light from the halogen lamp 41 in the lamp unit 40 (see FIG. 4). When the optical filter 43*b* to 43*f* enters the optical path of the light from the halogen lamp 41 during the period A, the amount of reference light starts to gradually increase. The amount of reference light then becomes constant when the optical path of the light from the halogen lamp 41 is completely within the optical filter 43*b* to 43*f*. As the optical filter 43*b* to 43*f* starts to deviate from the optical path of the light from the halogen lamp 41, the amount of reference light starts to gradually decrease, and the amount of reference light becomes 0 when the optical filter 43*b* to 43*f* is completely out of the optical path of the light from the halogen lamp 41.

As shown in FIG. 11, the reference light is converted to an electrical signal by the reference light photoelectric conversion element 72*e*, and the converted electrical signal is amplified by the reference light pre-amplifier 72*f* and the amplifier circuit 503. The signal (hereinafter referred to as reference signal) corresponding to the reference light is output from the amplifier circuit 503, which reference signal is then input to the differentiating circuit 504. The differential signal of the reference signal having the waveform indicated as "differential signal of reference signal" in FIG. 18 is generated by the differentiating circuit 504. The differential signal of the reference signal is input to the apparatus side control part 502 from the differentiating circuit 504 via a comparator (not shown).

In step S12 of FIG. 17, number of clocks N1 at the point the differential signal of the reference signal reaches a predetermined positive threshold value (+) is detected by the apparatus side control part 502. Specifically, the differential signal of the reference signal rises with increase in amount of reference light, as shown in FIG. 18. When the differential signal reaches a predetermined positive threshold value (+), a pulse signal that rises to H level in the comparator (not shown), to which the differential signal is input from the differentiating circuit 504 (see FIG. 12), is output. The pulse signal is input to the controller 502*a* of the apparatus side control part 502, and the number of clocks N1 at the point the pulse signal had risen to H level is detected in the controller 502a. The number of clocks N1 at the point the differential signal of the reference signal reaches the predetermined positive threshold value (+) is thus detected by the controller 502a of the apparatus side control part 502.

Subsequently, the amount of reference light further increases and becomes constant at a predetermined value, as shown in FIG. 18. The amount of reference light thereafter gradually decreases. Accompanied therewith, the differential signal of the reference signal gradually lowers. In step S13 of FIG. 17, the number of clocks (N2) at the point the differential signal of the reference signal reaches a predetermined negative threshold value (−) is detected by the apparatus side control part 502. Specifically, when the differential signal of the reference signal gradually lowers and reaches the predetermined negative threshold value (−), the pulse signal that rises to H level in the comparator (not shown), to which the differential signal is input from the differential circuit 504 (see FIG. 12), is output. The pulse signal is input to the controller 502a of the apparatus side control part 502, and the number of clocks N2 at the point that pulse signal had risen to H level is detected. The number of clocks N2 at the point the differential signal of the reference signal reaches the predetermined negative threshold value (−) is thus detected by the controller 502a of the apparatus side control part 502.

In step S14 of FIG. 17, the number of clocks (N clock) counted from the number of clocks N1 to the number of clocks N2 is calculated with the equation N=N2−N1 by the apparatus side control part 502. In step S15, the number of clocks (n clock) for determining the timing to start acquiring the signal corresponding to the transmitted light of the measurement specimen is calculated using the equation n=(N−m)/2 by the apparatus side control part 502. In the equation, m clock is the number of clocks set in advance as an appropriate period necessary for the apparatus side control part 502 to acquire the signal corresponding to the transmitted light of the measurement specimen.

In step S16, the number of clocks (P clock) from detection of the slit to the rise of the reference signal is calculated using the equation P=N1-N21 by the apparatus side control part 502 of the control substrate 5. In step S17, the number of clocks (p clock) for determining the timing to start acquiring the signal corresponding to the transmitted light of the measurement specimen is calculated using the equation p=P+n by the apparatus side control part 502. Therefore, in the first embodiment, the timing for the apparatus side control part 502 to start acquiring the signal corresponding to the transmitted light is calculated using the slits formed in the filter part 43.

As apparent from FIG. 18, the signal of the period in which the amount of light emitted from the lamp unit 40 is stable can be acquired by acquiring the signal from the detecting part 72 corresponding to the transmitted light of the measurement specimen for a period of m clock by the multiplexer 501a after p clock calculated in the above manner from N21 clock.

The process of step S3 of FIG. 16 will now be described in detail with reference to FIGS. 8, 12, 13, and 19 to 21.

Figure 19:
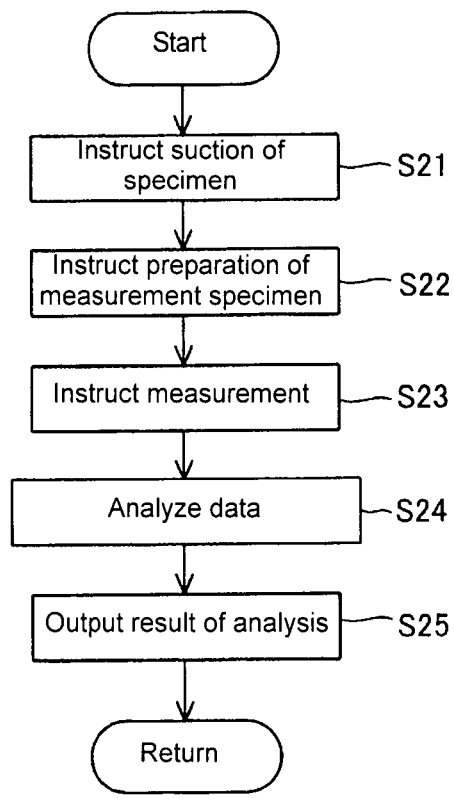
FIG. 19 is a flow chart showing the details (sub-routine) of the analyzing process by the control part of the control device in step S3 of FIG. 16.

First, in step S21 of FIG. 19, the suction of the specimen is instructed by the control part 4a. The specimen is thereby suctioned by the specimen dispensing arm 30 from the cuvette 250 held in the rotation conveyance section 20.

In step S22, preparation of the measurement specimen is instructed by the control part 4a. The specimen suctioned by the specimen dispensing arm 30 is thereby dispensed into a plurality of cuvettes 250 and the reagent for starting coagulation of the blood in the reagent container (not shown) is added to the specimen in the plurality of cuvettes 250 in the detection mechanism unit 2 by the reagent dispensing arm 50. The measurement specimen is thereby prepared. The cuvette 250 accommodating the measurement specimen is then moved to the insertion hole 71a of the cuvette mounting part 71 of the measurement section 70 by the cuvette transporting section 60.

In step S23, measurement is instructed by the control part 4a. The measurement of the measurement specimen thereby starts in the measurement section 70. The measurement will now be described in detail.

Light of five different types of wavelength characteristics (340 nm, 405 nm, 575 nm, 660 nm, and 800 nm) are sequentially and intermittently emitted from the lamp unit 40 to the cuvette 250 moved to the insertion hole 71a (see FIG. 8). The light that has passed the cuvette 250 is converted to digital data via the photoelectric conversion element 72b, the pre-amplifier 72c, the multiplexer 501a, the offset circuit 501b, the amplifier 501c, and the A/D converter 11d, and stored in the logger memory 502h.

The operation of the signal processing part 501 will now be described with reference to FIG. 13.

The processing of the electrical signal by the multiplexer 501a, the offset circuit 501b, the amplifier 501c, and the A/D converter 501d is performed partially in parallel in three signal processing lines L0 to L2 including the multiplexer 501a, the offset circuit 501b, the amplifier 501c, and the A/D converter 501d. That is, as shown in FIG. 13, the processing of the electrical signal by the multiplexer 501a, the offset circuit 501b, and the amplifier 501c in the signal processing line L0, and conversion process by the A/D converter 501d and data storing process to the logger memory 502h (see FIG. 12) of the apparatus side control part 502 in the signal processing line L1 are performed in parallel. Similarly, the processing of the electrical signal by the multiplexer 501a, the offset circuit 501b, and the amplifier 501c in the signal processing line L1, and conversion process by the A/D converter 501d and data storing process to the logger memory 502h (see FIG. 12) of the apparatus side control part 502 in the signal processing line L2 are performed in parallel. Moreover, the processing of the electrical signal by the multiplexer 501a, the offset circuit 501b, and the amplifier 501c in the signal processing line L2, and conversion process by the A/D converter 501d and data storing process to the logger memory 502h (see FIG. 12) of the apparatus side control part 502 in the signal processing line L0 are performed in parallel.

Figure 20:
FIG. 20 is a view showing a method of signal processing in the signal processing part of the blood coagulation analyzer according to the first embodiment of the present invention.
Figure 20:

As shown in FIG. 20, the partially parallel process of the electrical signal is performed in sections of 48 μsec sequentially using three signal processing lines L0 to L2. Specifically, in step S0 shown in FIG. 20, switching process to channel CH0 by the multiplexer 501a, correcting process by the offset circuit 501b, and amplifying process by the amplifier 501c are performed in the signal processing line L0. In step 0, the signal processing lines L1 and L2 are in a state (signal waiting process) of waiting for the electrical signal to stabilize, and thus the processing of the electrical signal is not performed. In step 1 of FIG. 20, switching process to channel CH16 by the multiplexer 501a, correcting process by the offset circuit 501b, and amplifying process by the amplifier 501c are performed in the signal processing line L1. In step 1, the signal processing lines L0 and L2 are in a state of waiting for the electrical signal to stabilize, and thus the processing of the electrical signal is not performed.

In step 2 of FIG. 20, A/D conversion process of the electrical signal of channel CH0 by the A/D converter 501*d* and data storing process to the logger memory 502*h* of signal processing line L0, switching process to channel CH32 by the multiplexer 501*a*, correcting process by the offset circuit 501*b*, and amplifying process by the amplifier 501*c* in the signal processing line L2 are performed in parallel. In step 2, the signal processing line L1 is in a state of waiting for the electrical signal to stabilize, and thus the processing of the electrical signal is not performed.

In step 3 of FIG. 20, switching process to channel CH1 by the multiplexer 501*a*, correcting process by the offset circuit 501*b*, and amplifying process by the amplifier 501*c* in the signal processing line L0 and A/D conversion process of the electrical signal of channel CH16 by the A/D converter 501*d* and data storing process to the logger memory 502*h* of signal processing line L1 are performed in parallel. In step 3, the signal processing line L2 is in a state of waiting for the electrical signal to stabilize, and thus the processing of the electrical signal is not performed.

In step 4 of FIG. 20, switching process to channel CH17 by the multiplexer 501*a*, correcting process by the offset circuit 501*b*, and amplifying process by the amplifier 501*c* in the signal processing line L1 and A/D conversion process of the electrical signal of channel CH32 by the A/D converter 501*d* and data storing process to the logger memory 502*h* of signal processing line L2 are performed in parallel. In step 4, the signal processing line L0 is in a state of waiting for the electrical signal to stabilize, and thus the processing of the electrical signal is not performed.

The parallel process similar to the processes in step 2 to step 4 is repeatedly performed while switching the channel of performing signal processing up to step 49 in the signal processing lines L0 to L2. In step 50, switching process to channel CH32 by the multiplexer 501*a*, correcting process by the offset circuit 501*b*, and amplifying process by the amplifier 501*c* in the signal processing line L2 are performed. In step 50, the signal processing lines L0 and L1 are in a state of waiting for the electrical signal to stabilize, and thus the processing of the electrical signal is not performed.

The multiplexer 501*a*, the offset circuit 501*b*, and the amplifier 501*c* all do not have stable output signal immediately after signal processing. In the first embodiment, a period of waiting for the electrical signal to stabilize is provided to prevent such unstable signals from being used in the analysis of the analyzing object.

As described above, the processing of the electrical signals of all channels CH0 to CH47 is performed in fifty-one steps of step 0 to 50. The processing the electrical signal by fifty-one steps is performed in the period of 2.45 msec (=48 μsec×51 steps). Furthermore, the processing of the electrical signal by fifty-one steps is performed once within the period of data acquiring process of m clock to be hereinafter described.

In the data storing process to the logger memory 502*h*, the data is stored in a predetermined address so that the optical filter that has transmitted the light from the halogen lamp 41 and the channel can be specified, as described above. The data stored in the logger memory 502*h* is then transmitted to the control part 4*a* at a predetermined timing.

Figure 21:
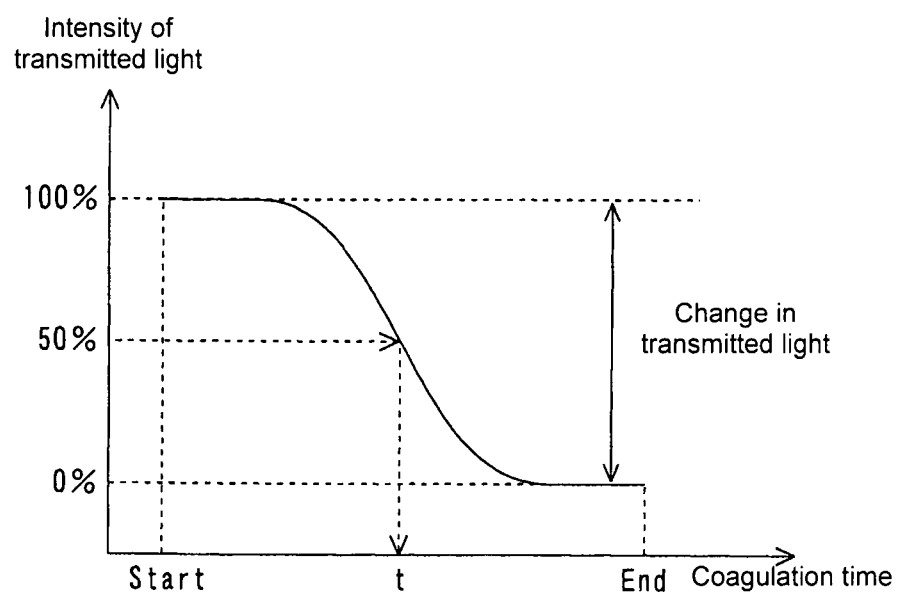
FIG. 21 is a graph showing a coagulation curve created by the blood coagulation analyzer according to the first embodiment of the present invention.

In step S24 of FIG. 19, the control part 4*a* selects the optical information (data) suited for analysis among the ten types of optical information (data) having different wavelength characteristics and amplification factor from the measurement section 70, that is, data of L gain and H gain corresponding to each five types of optical filters 43*b* to 43*f*, and analyzes the optical information. In step S25, the analysis result of the measurement specimen (coagulation curve and coagulation time as shown in FIG. 21 in the first embodiment) is output to the display part 4*b*.

The data acquiring process by the apparatus side control part 502 of the control substrate 5 of the first embodiment will now be described with reference to FIGS. 12, 18, and 22. The data acquiring process starts when the control part 4*a* instructs the analyzing process (step S3 of FIG. 16).

Figure 22:
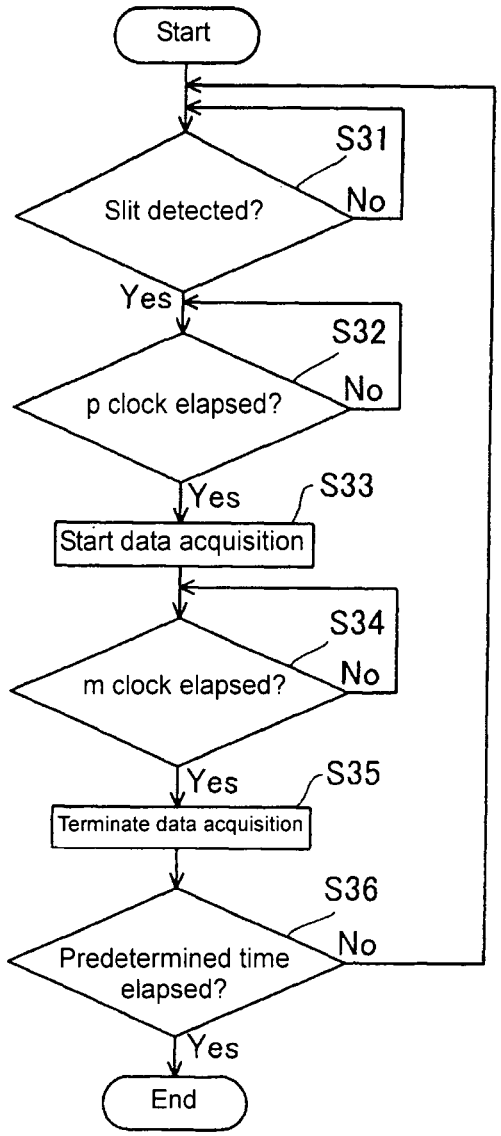
FIG. 22 is a flow chart describing the method of data acquiring process by the apparatus side control part of the first embodiment of the present invention.

In step S31 shown in FIG. 22, judgment is made whether or not the sensor 45 has detected the slit based on the signal from the sensor 45 by the apparatus side control part 502 (see FIG. 12). When slit is detected, a process of waiting for p clock (see FIG. 18) calculated in the initial setting to elapse from the point of slit detection is executed by the apparatus side control part 502 in step S32.

When p clock has elapsed from the detection of the slit, a process of starting the acquisition of digital data output from the three A/D converters 11*d* is executed by the apparatus side control part 502 in step S33. In step S34, a process of waiting for m clock to elapse from the start of acquisition of the digital data is executed by the apparatus side control part 502. When m clock has elapsed, the apparatus side control part 502 terminates the acquisition of the digital data in step S35. In step S36, a process of judging whether or not a predetermined time has elapsed from the reception of analysis instruction from the control part 4*a* is executed by the apparatus side control part 502. When the predetermined time has elapsed, the data acquiring process is terminated, and when the predetermined time has not elapsed, the process returns to the process of step S31.

The data acquiring process by the control part 4*a* of the control device 4 of the first embodiment will now be described with reference to FIGS. 2, 14, 19, 21, and 23. This process starts when the power of the control device 4 is turned ON.

Figure 23:
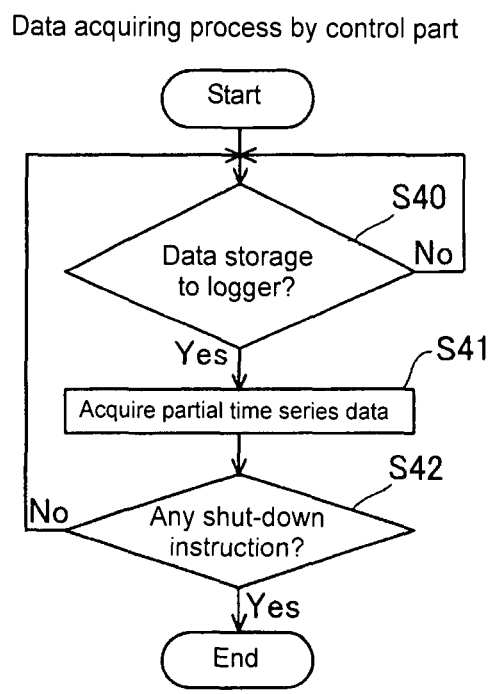
FIG. 23 is a flow chart describing the method of data acquiring process by the control part of the control device of the first embodiment of the present invention.

First, in step S40 of FIG. 23, the control part 4*a* monitors whether or not data is newly stored in the logger 502*h*, and waits until data worth 100 msec (one rotation of filter part 43) is stored. Specifically, when data worth 100 msec is accumulated in the logger 502*h*, the notification thereof is transmitted from the apparatus side control part 502, and thus the control part 4*a* waits for such notification to be transmitted. The data (partial time series data) worth 100 msec are acquired from the logger memory 502*h* via the interface 506 and the local bus interface 502*k* by the control part 4*a* in step S41. That is, as shown in FIG. 14, when data worth 100 msec corresponding to one rotation of the filter part 43 is accumulated in areas 0 to 5 of the logger memory 502*h*, the data accumulated in the areas 0 to 5 are acquired by the control part 4*a*.

In step S42, judgment on whether or not the control device 4 has received shut-down instruction is performed by the control part 4*a*. If the shut-down instruction is not received, the process returns to the process of step S40. If the shut-down instruction is received, the data acquiring process is terminated. When the data is acquired for the second time in step S41, the data of the six areas 6 to 11 following the areas 0 to 5 of the logger memory 502*h* from which data is acquired for the first time are acquired. Therefore, when data are acquired from the logger memory 502*h* by the control part 4*a*, the data for every six areas are sequentially acquired.

In the control part 4*a*, the partial time series data after the point the cuvette 250 (see FIG. 2) accommodating the measurement specimen is inserted in the insertion hole 71*a* of the measurement section 70 among the plurality of partial time series data acquired from the logger memory 502*h* in step S41 are combined in time series order, and predetermined time series data is created. Furthermore, in the control part 4a, the coagulation curve as shown in FIG. 21 is created based on the created time series data. The control part 4a then obtains the coagulation time of the measurement specimen from the created coagulation curve. Specifically, the point t at which the intensity of the transmitted light becomes 50%, which is the intermediate of 100% and 0%, is obtained in the graph of the coagulation curve shown in FIG. 21, and the elapsed time from the starting point of point t is calculated as the coagulation time. The coagulation time is displayed on the display part 4b in step S25 of FIG. 19, as described above.

In the first embodiment, since a plurality of photoelectric conversion elements 72b do not need to be arranged for each wavelength by receiving the light from the measurement specimen in the cuvette 250 irradiated with light of a plurality of wavelengths by the photoelectric conversion element 72b, complication and enlargement of the apparatus are suppressed. Furthermore, four types of measurement items of blood coagulation time measuring method, synthetic substrate measuring method, immunoturbidimetric measuring method, and platelet agglutination measuring method can be measured by irradiating light of wavelength 660 nm for blood coagulation time method, light of wavelength 405 nm for synthetic substrate measuring method, light of wavelength 800 nm for immunoturbidimetric measuring method, and light of wavelength 575 nm for platelet agglutination measuring method to the measurement specimen of the cuvette 250 held in the insertion hole 71a of the measurement section 70, and receiving the light from the measurement specimen at the photoelectric conversion element 72b.

In the first embodiment, light of four types of wavelengths are emitted intermittently over a plurality of times, as described above, and the analyzing items corresponding to the wavelengths of the light emitted over a predetermined reaction time can be analyzed from the plurality of results of measurement obtained by the light emitted over a plurality of times.

In the first embodiment, the four types of measurement items corresponding to the four types of wavelengths can be simultaneously measured by emitting the light of four types of wavelengths in a time sharing manner, as described above.

In the first embodiment, light of predetermined five different types of wavelengths can be extracted by sequentially arranging five types of optical filters 43b to 43f on the optical path of the light emitted from the halogen lamp 41 by rotating the filter part 43 arranged with five optical filters 43b to 43f with the motor, as described above. The plurality of extracted light of different wavelength may be guided to the measurement section 70 by the branched optical fibers 47. The measurement of four types of analyzing items (blood coagulation time measurement, synthetic substrate measurement, immunoturbidimetric measurement, and platelet agglutination measurement) then can be performed.

In the first embodiment, five types of light of different wavelengths are guided to the measurement section 70 from the light of one halogen lamp 41, as described above.

In the first embodiment, twenty insertions holes 71 are formed in the measurement section 70 and twenty photoelectric conversion elements 72b are arranged in each of the twenty-insert holes 71, as described above, whereby twenty measurement specimens can be simultaneously measured thereby enhancing the processing ability of the apparatus.

In the first embodiment, the blood coagulation time measurement, synthetic substrate measurement, immunoturbidimetric measurement, and platelet agglutination measurement may be performed by the transmitted light that has transmitted through the measurement specimen, as described above.

Second Embodiment

Figure 24:
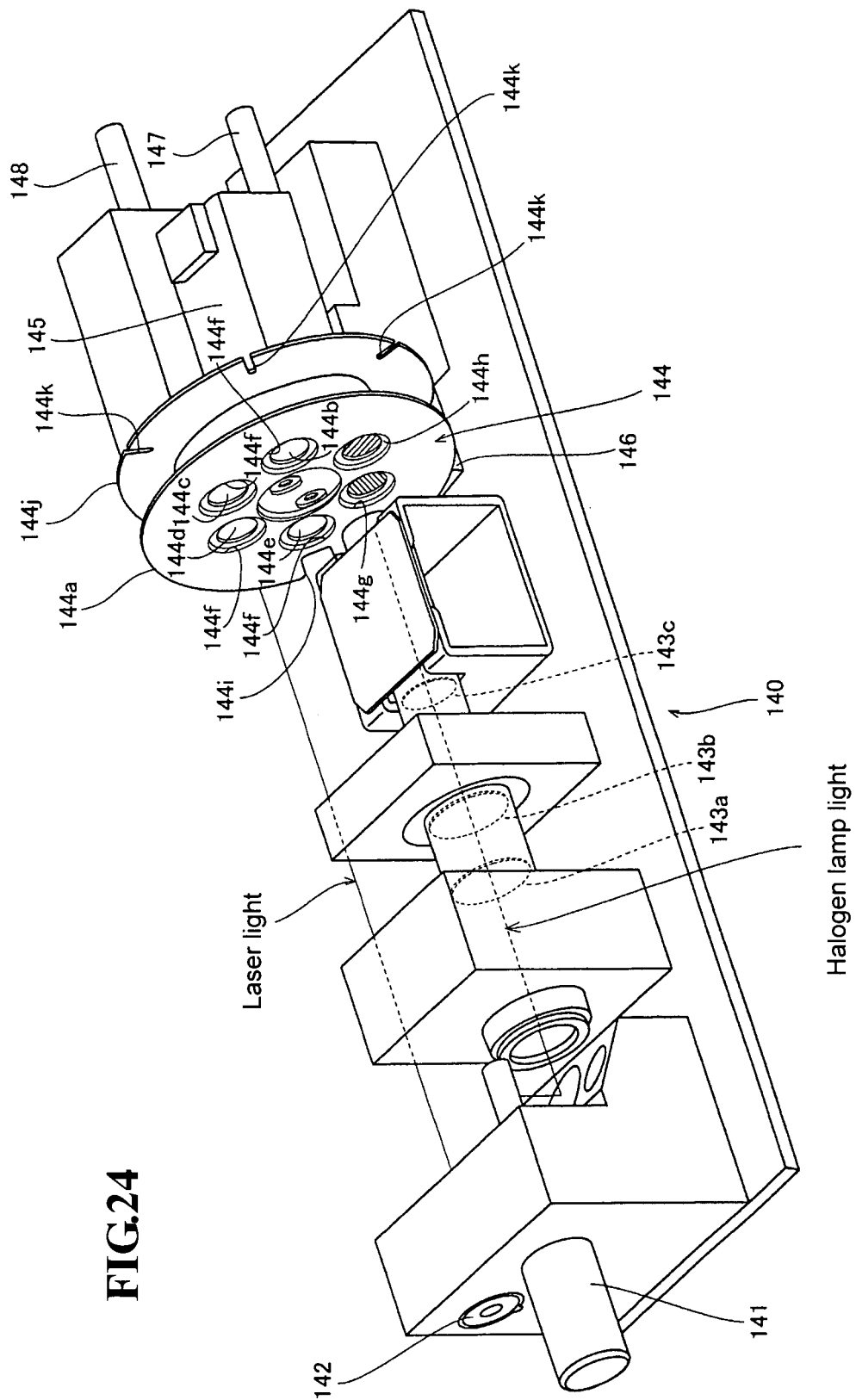
FIG. 24 is a perspective view showing a lamp unit of a blood coagulation analyzer according to a second embodiment of the present invention.
Figure 25:
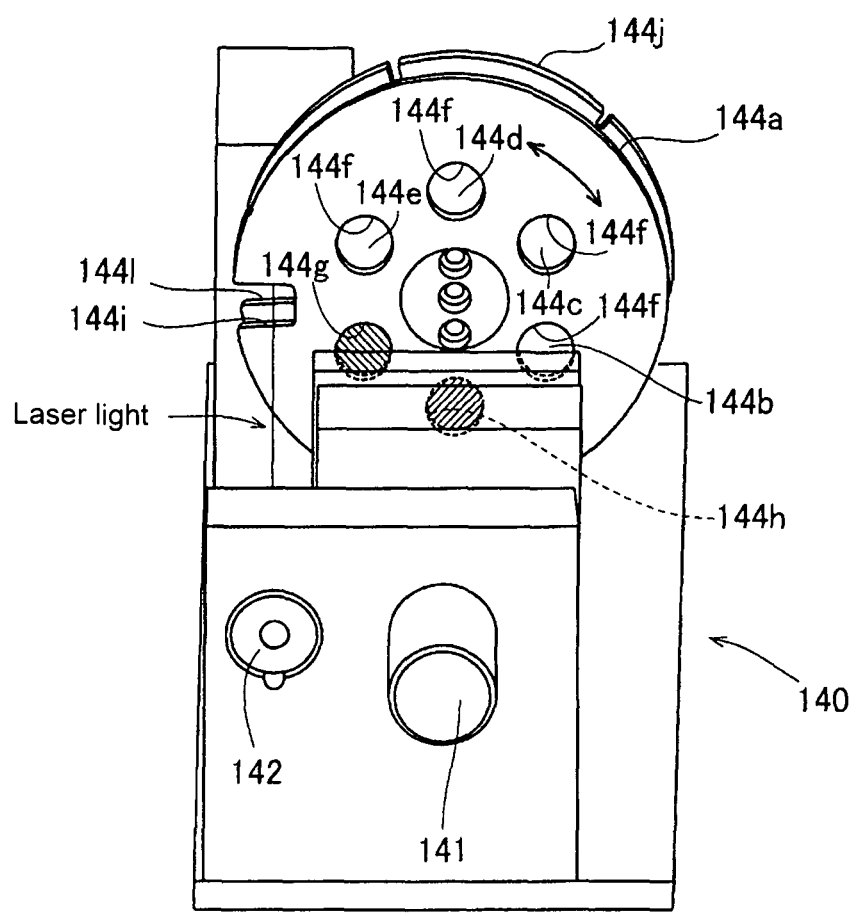
FIG. 25 is a perspective view seen from the front of the lamp unit of the blood coagulation analyzer according to the second embodiment of the present invention.
Figure 26:
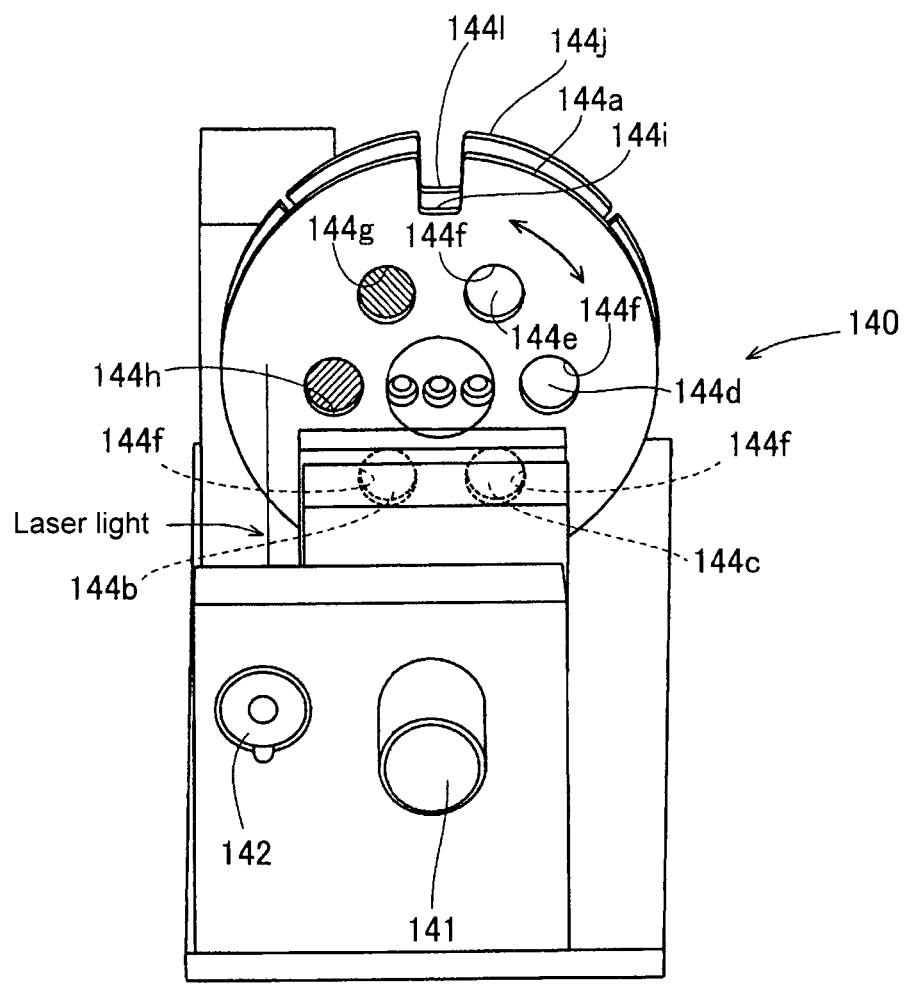
FIG. 26 is a perspective view seen from the front of the lamp unit of the blood coagulation analyzer according to the second embodiment of the present invention.
Figure 27:
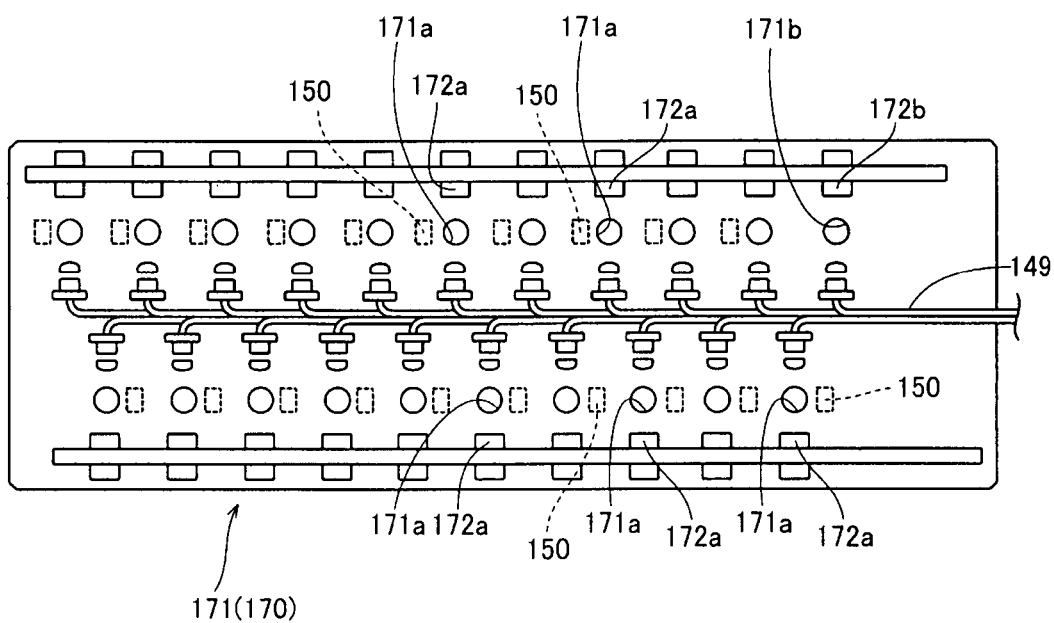
FIG. 27 is a schematic view describing an internal structure of a detecting part of a measurement section of the blood coagulation analyzer according to the second embodiment of the present invention.
Figure 28:
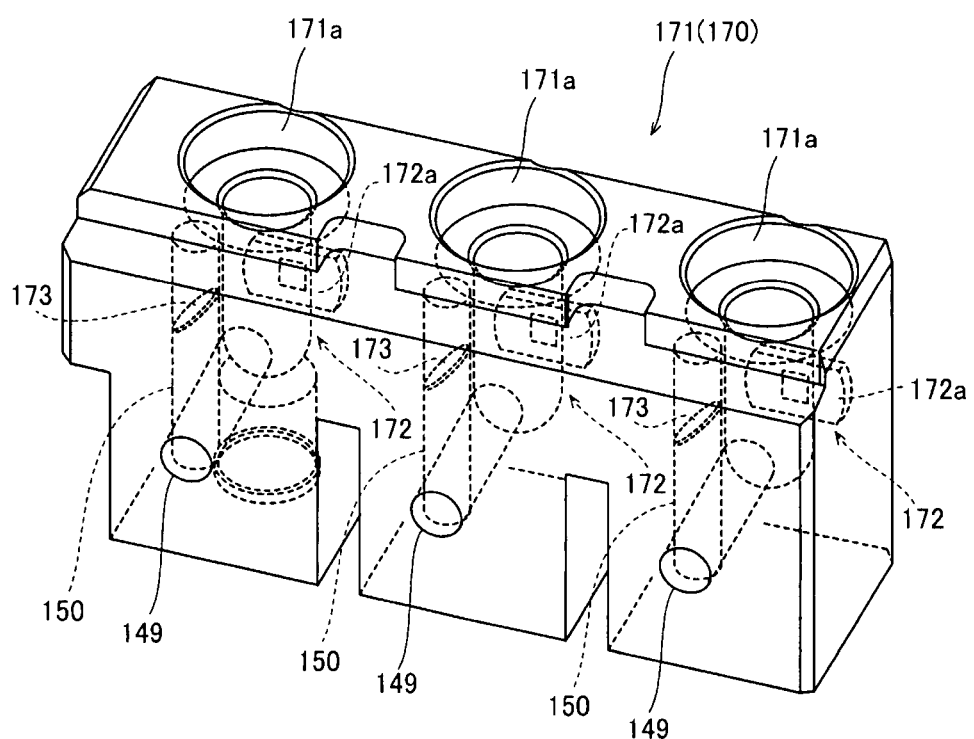
FIG. 28 is a perspective view describing the internal structure of the detecting part of the measurement section of the blood coagulation analyzer according to the second embodiment of the present invention.
Figure 29:
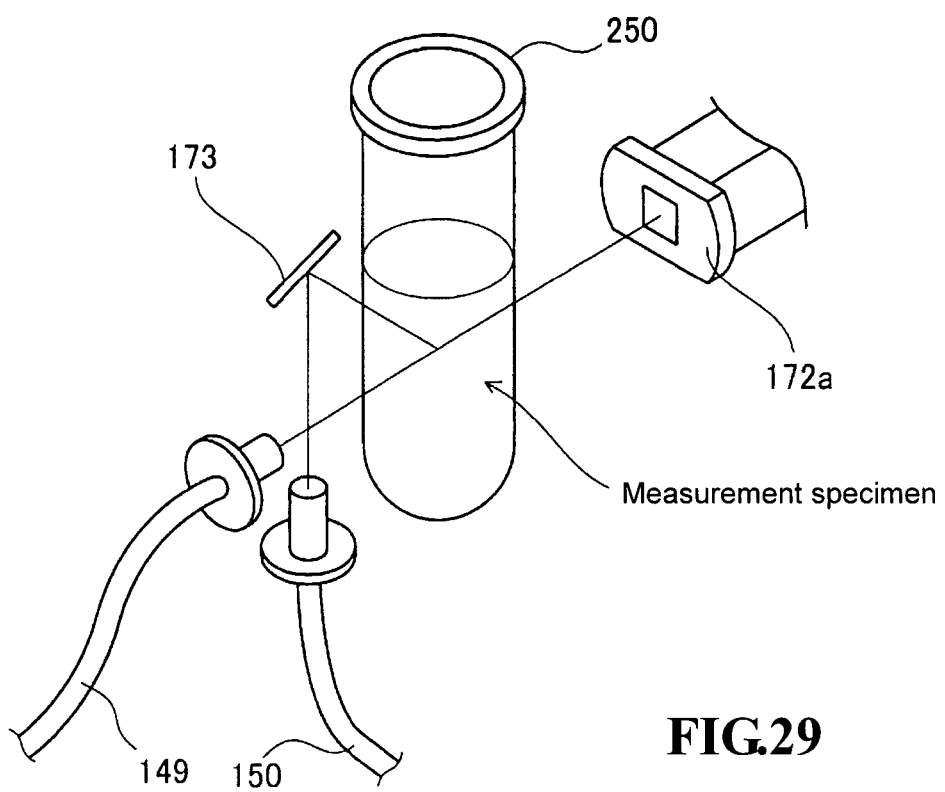
FIG. 29 is a frame format view describing the internal structure of the detecting part of the measurement section of the blood coagulation analyzer according to the second embodiment of the present invention.

FIGS. 24 to 26 are views describing in detail the lamp unit of the blood coagulation analyzer according to a second embodiment of the present invention. FIGS. 27 to 29 are views describing in detail the measurement section of the blood coagulation analyzer according to the second embodiment. An example where two light sources are arranged, and measurement is performed by scattered light from the specimen in the coagulation time method and measurement is performed by transmitted light from the specimen in the measuring methods other than the coagulation time method, as opposed to the first embodiment, will be described in the second embodiment with reference to FIGS. 24 to 29. Configurations other than the lamp unit 140 and the measurement section 170 in the second embodiment are the same as the first embodiment.

As shown in FIG. 24, the lamp unit 140 of the second embodiment is configured by a halogen lamp 141 serving as a light source, a laser light emitting element 142 that oscillates light of wavelength 660 nm, light collecting lenses 143a to 143c, a disc shaped filter part 144, a motor 145, a light transmission sensor 146, two optical fiber couplers 147 and 148, twenty-one branched optical fibers 149 (see FIG. 27), and twenty branched optical fibers 150 (see FIG. 27). The halogen lamp 141, the light collecting lenses 143a to 143c, the motor 145, and the light transmission sensor 146 respectively have configurations similar to the halogen lamp 41, the light collecting lenses 42a to 42c, the motor 44, and the sensor 45 of the first embodiment.

As shown in FIG. 24, the filter part 144 of the lamp unit 140 is configured to rotate with a motor shaft (not shown) of the motor 145 as the center. The filter part 144 includes a filter plate 144a arranged with four optical filters 144b to 144e of four light transmission characteristics (transparent wavelengths). Four holes 144f for attaching the four optical filters 144b to 144e, and holes 144g and 144h that are blocked so as not to transmit light are formed in the filter plate 144a. The four optical filters 144b to 144e having different light transmission characteristics (transparent wavelength) are respectively arranged in the four holes 144f. The blocked hole 144g is a spare hole, and a filter is attached thereto when additional filter becomes necessary. The light having a predetermined wavelength of the light from the halogen lamp 141 enters the optical fiber coupler 147 via the optical filters 144b to 144e. A slit 144i having the same size as an origin slit 144l of the slit plate 144j, to be hereinafter described, is formed in the filter plate 144a. The laser light from the laser light emitting element 142 enters the optical fiber coupler 148 via the origin slit 144l of the slit plate 144j and the slit 144i of the filter plate 144a.

The four optical filters 144b to 144e respectively transmits light of wavelength 340 nm, 405 nm, 575 nm, and 800 nm, and does not transmit light of other wavelengths. Therefore, the light that has passed through the four optical filters 144b to 144e have wavelength characteristic of 340 nm, 405 nm, 575 nm, and 800 nm.

In the second embodiment, the slit plate 144j having a size equal to the filter plate 144a is arranged on the side opposite to the halogen lamp 141 of the filter plate 144a. Six slits are formed in the slit plate 144j at a predetermined angular spacing (equally spaced at 60° in the second embodiment) along the circumferential direction. One of the six slits is an origin slit 144l having a slit width in the rotating direction of the filter part 144 larger than the other five normal slits 144k. The origin slit 144l and the normal slits 144k are formed at a predetermined angular spacing (equally spaced at 60° in the second embodiment) at an intermediate angle position between the four holes 144h and the blocked holes 144g and 144h of the filter plate 144a. The rotation of the filter part 144 is monitored with the origin slit 144l, the normal slits 144k, and the sensor 146.

In the second embodiment, with the rotation of the filter plate 144a, four optical filters 144b to 144e having different light transmission characteristics and one spare hole 144g are intermittently arranged in order on the optical path of the light collected by the light collecting lenses 143a to 143c. In this case, the laser light from the laser light emitting element 142 is shielded by the filter plate 144a, as shown in FIG. 26. As shown in FIG. 25, when the light shielded hole 144h is arranged on the optical path of the light collected by the light collecting lenses 143a to 143c, the slit 144i of the filter plate 144a and the origin slit 144l of the slit plate 144j are arranged on the optical path of the laser light from the laser light emitting element 142. The light of 660 nm from the laser light emitting element 142, and the light having predetermined wavelengths (340 nm, 405 nm, 575 nm, and 800 nm) of the light from the halogen lamp 141 thus enter the optical fiber coupler 147 or 148 in a time sharing manner.

The optical fiber couplers 147 and 148 are respectively adapted to enter the incident light to the twenty-one branched optical fibers 149 and the twenty optical fibers 150. The tips of the twenty-one branched optical fibers 140 and the twenty optical fibers 150 are connected to the measurement section, as shown in FIG. 27. As shown in FIGS. 27 and 29, the twenty-one branched optical fibers 149 are each arranged to apply light to the twenty insertion holes 171a and one reference light measurement hole 171b, to be hereinafter described, of the measurement section 170. The twenty branched optical fibers 150 are each arranged to apply light to the twenty insertion holes 171a of the measurement section 170.

The measurement section 170 includes a cuvette mounting part 171 and a detecting part 172. The cuvette mounting part 171 includes twenty insertion holes 171a to which the cuvette 250 accommodating the measurement specimen is inserted and one reference light measurement hole 171b. The detecting part 172 includes twenty photoelectric conversion elements 172a and one reference light photoelectric conversion element 172b in correspondence to the twenty insertion holes 171a and one reference light measurement hole 171b.

As shown in FIGS. 28 and 29, the tips of the branched optical fibers 149 on the measurement section 170 side are respectively arranged facing the twenty photoelectric conversion elements 172a and one reference light photoelectric conversion element 172b. In performing measurement through synthetic substrate method, immunoturbidimetric method, and platelet agglutination method, the light (light having specific wavelength characteristics by the plurality of filters) from the tip of the branched optical fibers 149 on the measurement section 170 side is irradiated on the cuvette 250 from the side surface of the insertion hole 171a, which light then transmits through the measurement specimen in the cuvette 250 and enters the photoelectric conversion element 172 so that transmitted light of the light having specific wavelength characteristics by the plurality of filters (light having wavelength of 340 nm, 405 nm, 575 nm, and 800 nm) is measured.

In the second embodiment, the tips of the twenty branched optical fibers 150 are respectively arranged facing vertically upward from the lower side of the twenty insertion holes 171a. A mirror 173 for reflecting the light is arranged in the vicinity of the insertion hole 171a at a position corresponding to the distal ends of the branched optical fibers 150. In measuring through coagulation time method, the light (laser light having wavelength characteristics of 660 nm) from the tip of the branched optical fibers 150 is irradiated on the cuvette 250 from the side surface of the insertion hole 171a by the mirror 173, which light then enters the measurement specimen in the cuvette 250 and the light scattered by the measurement specimen is detected by the photoelectric conversion element 172a.

In the second embodiment, the measurement by coagulation time method (blood coagulation time measurement) is carried out with scattered light, and measurement by synthetic substrate method, measurement by immunoturbidimetric method, and measurement by platelet agglutination method are carried out with transmitted light.

Therefore, in the second embodiment, the blood coagulation time measurement is carried out with the scattered light, and the measurement by synthetic substrate method, the measurement by immunoturbidimetric method, and the measurement by platelet agglutination method are carried out with transmitted light by guiding the light from the halogen lamp 141 and the light from the laser light emitting element 142 respectively to the insertion hole 171a by the branched optical fibers 149 and the branched optical fibers 150, as described above.

The embodiments disclosed herein are merely illustrative and should not be construed as being exclusive. Therefore, the present invention is shown by the scope of the claims, and is restricted in no way by the embodiment as described above; the present invention may be modified within the scope and equivalence of the appended claims.

Figure 30:
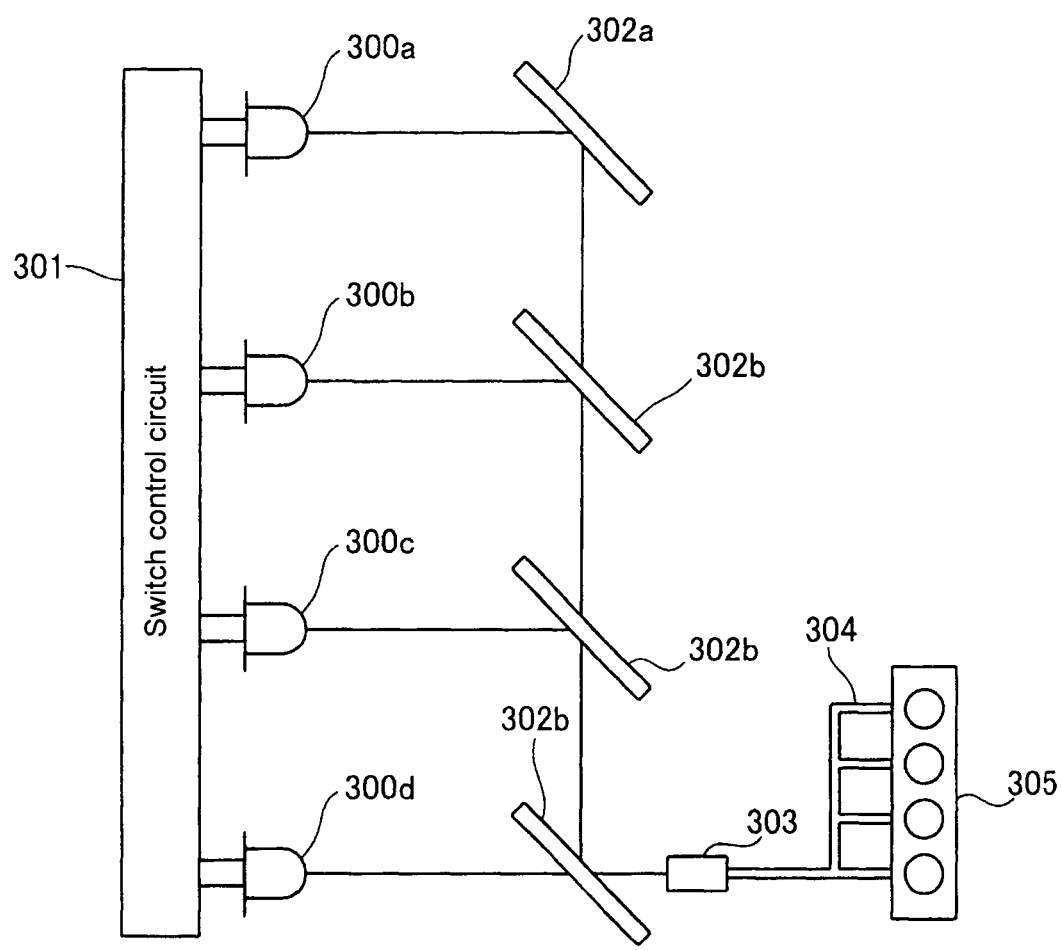
FIG. 30 is a frame format view of a first variant of the first embodiment of the present invention.

For instance, an example of rotating the filter part 43 arranged with five optical filter 43b to 43f to sequentially arrange five optical filters 43b to 43f on the optical path of the light from the halogen lamp 41 so as to extract light of a plurality of wavelengths has been described in the first embodiment, but the present invention is not limited thereto, and the timing of light emission of a plurality of light sources 300a to 300d may be electrically switch controlled as in the first variant shown in FIG. 30. In the first variant, four light sources 300a to 300d are arranged, which four light sources 300a to 300d respectively includes a laser light emitting element or LED that emits light having specific wavelength characteristics (e.g., light having wavelength of 660 nm for coagulation time measurement, light having wavelength of 405 nm for synthetic substrate measurement, light having wavelength of 800 nm for immunoturbidimetric measurement, and light having wavelength of 575 nm for platelet agglutination measurement). The four light sources 300a to 300d are controlled so as to electrically emit light in order by a switch control circuit 301. The light emitted from the four light sources 300a to 300d enter the optical fiber coupler 303 by means of a mirror 302a and dichroic mirrors 302b, and is guided from the optical fiber coupler 303 to a measurement section 305 via a branched optical fiber 304. Since the light of four types of wavelengths is sequentially guided to the measurement section 305 in such configuration as well, measurement of four types of measurement items (coagulation time measurement etc.) can be carried out.

In the configuration shown in the first variant, the switch control circuit 301 may be controlled to continuously emit light from one light source. A more accurate result of measurement can be obtained by carrying out the coagulation time measurement by continuously light emitting the light source 300a that emits light of wavelength 660 nm, for example.

Figure 31:
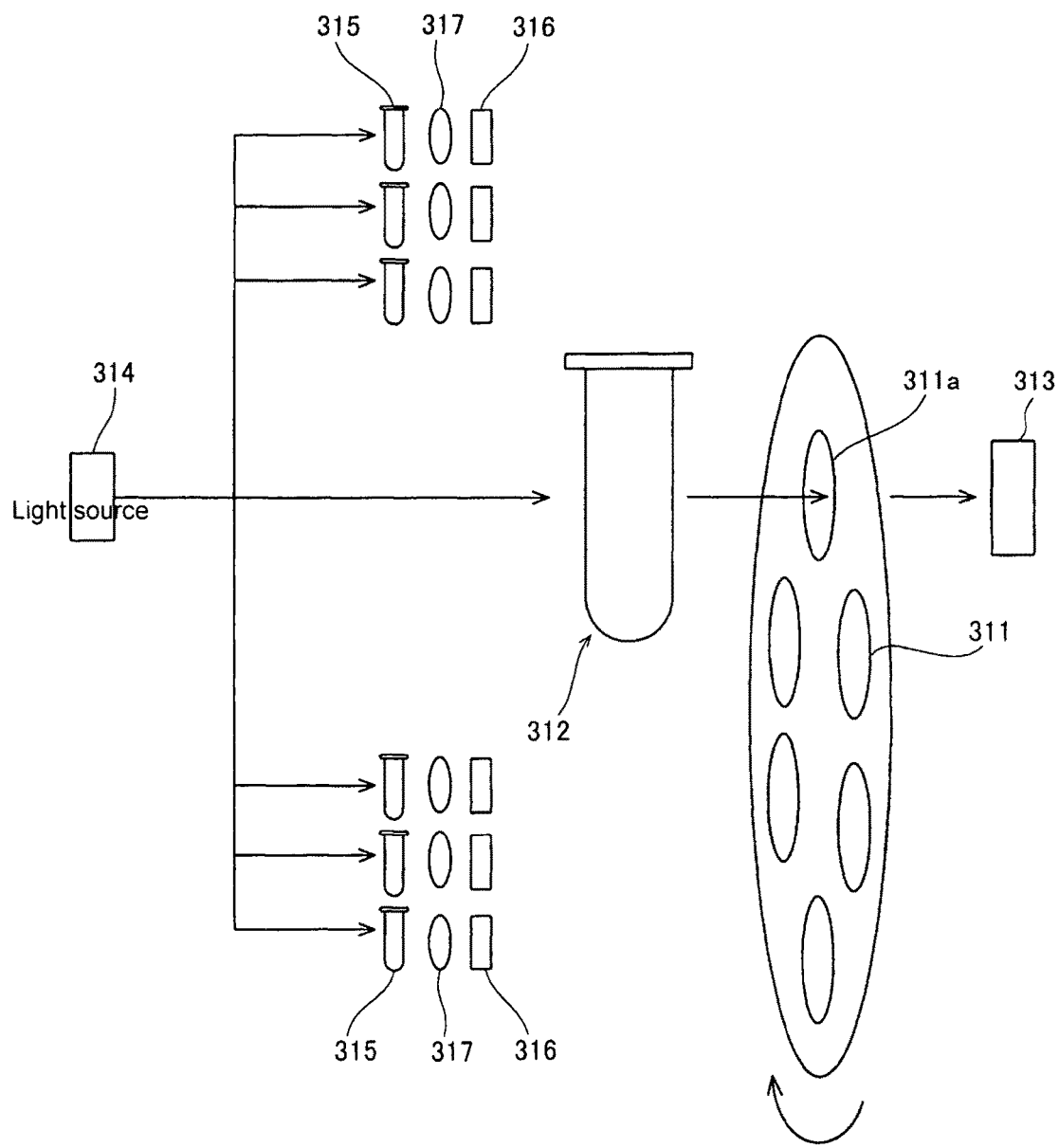
FIG. 31 is a frame format view of a second variant of the first embodiment of the present invention.

An example where the light of specific wavelength extracted by the filter part is irradiated on the measurement specimen has been described in the first embodiment and the second embodiment, but the present invention is not limited thereto, and the filter part 311 may be arranged between a measurement specimen 312 and a light receiving section 313, as shown in a second variant illustrated in FIG. 31. In the second variant, the light emitted from a light source 314 is irradiated on a measurement specimen 312, and the transmitted light or the scattered light from the measurement specimen 312 is received by the light receiving section 313 via a rotatable filter part 311 arranged with a plurality of filters 311a. Furthermore, a fixed filter 317 for extracting light of specific wavelength is arranged between other measurement specimens 315 and a light receiving section 316. A plurality of measurement items can be measured with such configuration.

An example where the control device 4 is arranged separate from the apparatus main body (detection mechanism unit 2 and conveyance mechanism unit 3) of the blood coagulation analyzer 1 has been described in the first and second embodiments, but the present invention is not limited thereto, and the control device 4 and the apparatus main body (detection mechanism unit 2 and conveyance mechanism unit 3) of the blood coagulation analyzer 1 may be integrated.

An example where twenty insertion holes 71a and 171a are provided has been described in the first and second embodiments, but the present invention is not limited thereto, and more than or less than twenty insertion holes may be formed.

An example where a spare hole 144g of the filter part 144 is blocked has been described in the second embodiment, but the present invention is not limited thereto, and an optical filter that transmits light of wavelength 660 nm, which is the same as the light emitted by the laser light emitting element 142, may be attached to the spare hole 144g. According to such configuration, the light for coagulation time measurement having wavelength of 660 nm can be irradiated on the measurement specimen not only from the branched optical fibers 150 but also from the branched optical fibers 149, and thus the coagulation time measurement can be carried out with both transmitted light and scattered light.

What is claimed is:
1. A blood coagulation analyzer comprising:
a light source;
an optical extracting unit comprising a plurality of optical filters, wherein the plurality of optical filters comprise a first filter that filters light so as to transmit a first light suitable for use in a measurement performed according to a blood coagulation time method, a second filter that filters light so as to transmit a second light suitable for use in a measurement performed according to a synthetic substrate method, and a third filter that filters light so as to transmit a third light suitable for use in a measurement performed according to an immunoturbidimetric method, the optical extracting unit configured to sequentially and repeatedly pass the plurality of filters through light emanating from the light source;
and a plurality of measurement sections each comprising an individual light emitting unit, an individual reaction container holder configured to hold a reaction container containing a measurement specimen that is a mixture of a blood specimen and a reagent, and an individual light receiving unit arranged such that when a reaction container containing a measurement specimen to be measured by the blood coagulation time method is held in the individual reaction container holder, light emitted from the individual light emitting unit travels through only one reaction container holder, which is contained in the reaction container held in the individual reaction container holder, and then into the individual light receiving unit;
wherein the number of the plurality of measurement sections is greater than the number of the plurality of optical filters;
wherein each individual light receiving unit comprises a photoelectric conversion element,
wherein the light source, optical extracting unit, and plurality of measurement sections are arranged within the blood coagulation analyzer such that light emitted from the light source travels through the optical extracting unit and then into each of the plurality of measurement sections, where the first light is emitted through the individual light emitting unit in each measurement section at a same time, the second light is emitted through the individual light emitting unit in each measurement section at a same time, and the third light is emitted through the individual light emitting unit in each measurement section at a same time, when the measurement specimen to be measured by the blood coagulation time method is present;
further comprising an analyzing section configured to obtain a first plurality of partial time series data regarding a blood coagulation time method when the light receiving unit receives the first light transmitted through the measurement specimen, a second plurality of partial time series data regarding a synthetic substrate method when the light receiving unit receives the second light transmitted through the measurement specimen, and a third plurality of partial time series data regarding an immunoturbidimetric method when the light receiving unit receives the third light transmitted through the measurement specimen;
the analyzing section configured to create first complete time series data by combining in time series order the first partial time series data, second complete time series data by combining in time series order the second partial time series data, and third complete time series data by combining in time series order the third partial time series data, and generate a measurement result of the blood coagulation time method based on the first complete time series data,
the analyzing section configured to create the first, second, and third complete time series data separately.
2. The blood coagulation analyzer according to claim 1, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.
3. The blood coagulation analyzer according to claim 1, wherein the light source comprises a halogen lamp.

4. The blood coagulation analyzer according to claim 1, wherein the plurality of optical filters comprise further comprises a fourth filter that filters light suitable for use in measurement by platelet agglutination method,
wherein the analyzing section is further configured to obtain a plurality of partial time series data regarding a platelet agglutination method when a light receiving unit receives light suitable for use in a measurement performed according to a platelet agglutination method, to create time series data for the platelet agglutination method by combining in time series order each of the partial time series data regarding the platelet agglutination method, and to generate results of the platelet agglutination method based on the time series data regarding the platelet agglutination method.

5. The blood coagulation analyzer according to claim 4, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.

6. The blood coagulation analyzer according to claim 1, wherein the analyzing section is configured to generate a graph by plotting the first complete time series data.

7. A blood coagulation analyzer comprising:
a light source;
an optical extracting unit comprising a plurality of optical filters, wherein the plurality of optical filters comprise a first filter that filters light so as to transmit a first light suitable for use in a measurement performed according to a blood coagulation time method, a second filter that filters light so as to transmit a second light suitable for use in a measurement performed according to a synthetic substrate method, and a third filter that filters light so as to transmit a third light suitable for use in a measurement performed according to an immunoturbidimetric method, the optical extracting unit configured to sequentially and repeatedly pass the plurality of filters through light emanating from the light source;
and a plurality of measurement sections each comprising an individual light emitting unit, an individual reaction container holder configured to hold a reaction container containing a measurement specimen that is a mixture of a blood specimen and a reagent, and an individual light receiving unit arranged such that when the reaction container containing a measurement specimen for a measurement by a synthetic substrate method is held in the individual reaction container holder, light emitted from the individual light emitting unit travels through only one reaction container holder, which is contained in the reaction container held in the individual reaction container holder, and then into the individual light receiving unit;
wherein the number of the plurality of measurement sections is greater than the number of the plurality of optical filters;
wherein each individual light receiving unit comprises a photoelectric conversion element;
wherein the light source, optical extracting unit, and plurality of measurement sections are arranged within the blood coagulation analyzer such that light emitted from the light source travels through the optical extracting unit and then into each of the plurality of measurement sections, where the first light is emitted through the individual light emitting unit in each measurement section at a same time, the second light is emitted through the individual light emitting unit in each measurement section at a same time, and the third light is emitted through the individual light emitting unit in each measurement section at a same time, when the measurement specimen to be measured by the synthetic substrate method is present;
further comprising an analyzing section configured to obtain a first plurality of partial time series data regarding a blood coagulation time method when the light receiving unit receives the first light transmitted through the measurement specimen, a second plurality of partial time series data regarding a synthetic substrate method when the light receiving unit receives the second light transmitted through the measurement specimen, and a third plurality of partial time series data regarding an immunoturbidimetric method when the light receiving unit receives the third light transmitted through the measurement specimen;
the analyzing section configured to create first complete time series data by combining in time series order the first partial time series data, second complete time series data by combining in time series order the second partial time series data, and third complete time series data by combining in time series order the third partial time series data, and generate a measurement result of the synthetic substrate method based on the second complete time series data,
the analyzing section configured to create the first, second, and third complete time series data separately.

8. The blood coagulation analyzer according to claim 7, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.

9. The blood coagulation analyzer according to claim 7, wherein the light source comprises a halogen lamp.

10. The blood coagulation analyzer according to claim 7, wherein the plurality of optical filters comprise further comprises a fourth filter that filters light suitable for use in measurement by platelet agglutination method,
wherein the analyzing section is further configured to obtain a plurality of partial time series data regarding a platelet agglutination method when a light receiving unit receives light suitable for use in a measurement performed according to a platelet agglutination method, to create time series data for the platelet agglutination method by combining in time series order each of the partial time series data regarding the platelet agglutination method, and to generate results of the platelet agglutination method based on the time series data regarding the platelet agglutination method.

11. The blood coagulation analyzer according to claim 10, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.

12. The blood coagulation analyzer according to claim 7, wherein the analyzing section is configured to generate a graph by plotting the second complete time series data.

13. A blood coagulation analyzer comprising:
a light source;
an optical extracting unit comprising a plurality of optical filters, wherein the plurality of optical filters comprise a first filter that filters light so as to transmit a first light suitable for use in a measurement performed according to a blood coagulation time method, a second filter that filters light so as to transmit a second light suitable for use in a measurement performed according to a synthetic substrate method, and a third filter that filters light so as to transmit a third light suitable for use in a measurement performed according to an immunoturbidimetric method, the optical extracting unit configured to sequentially and repeatedly pass the plurality of filters through light emanating from the light source;
and a plurality of measurement sections each comprising an individual light emitting unit, an individual reaction container holder configured to hold a reaction container containing a measurement specimen that is a mixture of a blood specimen and a reagent, and an individual light receiving unit arranged such that when a reaction container containing a measurement specimen for a measurement by an immunoturbidimetric method is held in the individual reaction container holder, light emitted from the individual light emitting unit travels through only one reaction container holder, which is contained in the reaction container held in the individual reaction container holder, and then into the individual light receiving unit;
wherein the number of the plurality of measurement sections is greater than the number of the plurality of optical filters;
wherein each individual light receiving unit comprises a photoelectric conversion element;
wherein the light source, optical extracting unit, and plurality of measurement sections are arranged within the blood coagulation analyzer such that light emitted from the light source travels through the optical extracting unit and then into each of the plurality of measurement sections, where the first light is emitted through the individual light emitting unit in each measurement section at a same time, the second light is emitted through the individual light emitting unit in each measurement section at a same time, and the third light is emitted through the individual light emitting unit in each measurement section at a same time, when the measurement specimen to be measured by the immunoturbidimetric method is present;
further comprising an analyzing section configured to obtain a first plurality of partial time series data regarding a blood coagulation time method when the light receiving unit receives the first light transmitted through the measurement specimen, a second plurality of partial time series data regarding a synthetic substrate method when the light receiving unit receives the second light transmitted through the measurement specimen, and a third plurality of partial time series data regarding an immunoturbidimetric method when the light receiving unit receives the third light transmitted through the measurement specimen;
the analyzing section configured to create first complete time series data by combining in time series order the first partial time series data, second complete time series data by combining in time series order the second partial time series data, and third complete time series data by combining in time series order the third partial time series data, and generate a measurement result of the immunoturbidimetric method based on the third complete time series data,
the analyzing section configured to create the first, second, and third complete time series data separately.

14. The blood coagulation analyzer according to claim 13, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.

15. The blood coagulation analyzer according to claim 13, wherein the light source comprises a halogen lamp.

16. The blood coagulation analyzer according to claim 13, wherein the plurality of optical filters comprise further comprises a fourth filter that filters light suitable for use in measurement by platelet agglutination method,
wherein the analyzing section is further configured to obtain a plurality of partial time series data regarding a platelet agglutination method when a light receiving unit receives light suitable for use in a measurement performed according to a platelet agglutination method, to create time series data for the platelet agglutination method by combining in time series order each of the partial time series data regarding the platelet agglutination method, and to generate results of the platelet agglutination method based on the time series data regarding the platelet agglutination method.

17. The blood coagulation analyzer according to claim 16, further comprising a processor, memory, and a program that controls the optical extracting unit so that the optical filters are sequentially disposed a plurality of times in an optical path of the light source in a time sharing manner,
wherein partial time series data is collected by the analyzing section over each of the plurality of times that the optical filters are disposed in an optical path of the light source.

18. The blood coagulation analyzer according to claim 13, wherein the analyzing section is configured to generate a graph by plotting the third complete time series data.

* * * * *